United States Patent [19]

Spector et al.

[11] Patent Number: 5,432,172
[45] Date of Patent: Jul. 11, 1995

[54] BIOLOGICAL APPLICATIONS OF ALKALOIDS DERIVED FROM THE TUNICATE EUDISTOMA SP.

[75] Inventors: Ilan Spector; Nava R. Shochet, both of Port Jefferson, N.Y.; Yoel Kashman, Tel-Aviv, Israel; Amira Rudi, Ramat Hasharon, Israel; Gary Gellerman, Holon, Israel

[73] Assignee: The Research Foundation of State University of New York, Albany, N.Y.

[21] Appl. No.: 28,322

[22] Filed: Mar. 9, 1993

Related U.S. Application Data

[63] Continuation-in-part of Ser. No. 924,194, Aug. 3, 1992, Pat. No. 5,278,168.

[51] Int. Cl.$^6$ .............................................. A61K 31/54
[52] U.S. Cl. ..................................................... 514/224.5
[58] Field of Search ........................................ 514/224.5

[56] References Cited

U.S. PATENT DOCUMENTS 4,857,538  8/1989  Kashman et al. .
5,278,168  1/1994  Spector et al. ............... 514/279

OTHER PUBLICATIONS

Kaul et al., *Ann. Rev. Pharmacol.*, 26, 117–142 (1986).
Scheuer, *Science*, 248, 173–177 (1990).
Spector et al., *Science*, 214, 493–495 (1983).
Coue et al., *FEBS Lett.*, 213, 316–318 (1987).
Spector et al., *Cell Motility and the Cytoskeleton*, 13, 127–4 (1989).
Rudi et al., *Tet. Lett.*, 29, 6655–6656 (1988).
Rudi et al., *Tet. Lett.*, 29, 3861–3862 (1988).
Rudi et al., *J. Org. Chem.*, 54, 5331–5337 (1989).
Schmitz et al., *J. Am. Chem. Soc.*, 105, 4835–4837 (1983).
Bloor et al., *J. Am. Chem. Soc.*, 109, 6134–6136 (1987).
Cooray et al., *J. Org. Chem.*, 53, 4619–4620 (1988).
Kobayashi et al., *J. Org. Chem.*, 53, 1800–1804 (1988).
Kobayashi et al., *Tet. Lett.*, 29, 1177–1180 (1988).
Charyulu et al., *Tet. Lett.*, 30, 4201–4202 (1989).
Molinski et al., *J. Org. Chem.*, 54, 4256–4259 (1989).
Schmitz et al., *J. Org. Chem.*, 56, 804–808 (1991).
Lockwood et al., *J. Cell. Biochem.*, 33, 237–255 (1987).
Willingham, *Int. Rev. Cytol.*, 44, 319–363 (1976).

(List continued on next page.)

*Primary Examiner*—Johann Richter
*Assistant Examiner*—John Peabody
*Attorney, Agent, or Firm*—Hoffmann & Baron

[57] ABSTRACT

Biological applications of synthetic and natural alkaloids derived from the tunicate Eudistoma sp. are disclosed. A method regulating cell growth includes contacting one or more cells with an effective concentration of a compound for regulating cell growth. These compounds include: Segoline A, Segoline B, Isosegoline A, Norosegoline, Debromoshermilamine, Eilatin, 4-methylpyrido[2,3,4-kl]acridine, pyrido[2,3,4-kl]acridine, 1-acetyl-2,6-dimethylpyrido[2,3,4-kl]acridine, and derivatives and combinations of these compounds. An effective concentration range for using these compounds can range from approximately 0.1 μM to 100 μM. The effective concentration range for Eilatin, the most potent of these compounds is from 0.01 μM to 0.99 μM, and the effective concentration range for the other compounds of the present invention is from about 1.0 μM to 100 μM. The method has been shown to suppress growth of tumor cells, to induce differentiation of the tumor cells, and induce reverse transformation of the tumor cells. In transformed cells, the method induces reverse transformation. The method also inhibits the proliferation of cells. The examples show that the method of the present invention affects cyclic AMP mediated biological processes. At the effective concentrations this method affects the cyclic AMP mediated biological processes of cells to achieve the results described above.

28 Claims, 21 Drawing Sheets

OTHER PUBLICATIONS

Schubert, *Developmental Biology of Cultured Nerve, Muscle, and Gila,* John Wiley & Sons, New York (1984).
Katsaros et al., *FEBS Lett.,* 223, 97-103 (1987).
Tagliaferri et al., *Cancer Res.,* 48, 1642-1650 (1988).
Tortora et al., *Proc. Natl. Acad. Sci. USA,* 87, 705-708 (1990).
Pilkis et al., *Annu. Rev. Nutr.,* 11, 465-515 (1991).
Maghrabi et al., *J. Biol. Chem.,* 257, 233 (1982).
Hod et al., *J. Biol. Chem.,* 259, 15603-15608 (1984).
Granner et al., *J. Biol. Chem., 265, 10173-10176 (1990).*
Bilezikjian et al., *Endocrinology,* 113, 1726-1731 (1983).
Ray et al., *Mol. Cell. Endocrinology,* 45, 175-182 (1986).
Gabriel et al., *Neuroendocrinology,* 50, 170-176 (1989).
Carroll et al., *J. Org. Chem.,* 54, 4231-4232 (1989).
Amano et al., *Proc. Natl. Acad. Sci. USA,* 63, 258-263 (1972).
Spector, "Electrophysiology of clonal nerve cell lines", in: *Excitable Cells in Tissue Culture,* Nelson et al., eds., Plenum, N.Y., 247-277 (1981).
Hynes et al., *Cell,* 13, 151-163 (1978).
Hod et al., *N.Y. Acad. Sci.,* 478, 31-45 (1986).
Hod et al., *J. Biol. Chem.,* 263, 7747-7752 (1988).
Vine et al., *Red Sea Invertebrates,* Ch. 10, 209-210, Immel Publishing (1986).
Rinehart, Jr., et al., *J. Am. Chem. Soc.,* 109, 3378-3387 (1987).
Rinehart, Jr., et al., *Pure & Appl. Chem.,* 53, 795-817 (1981).
Schmitz et al., *J. Am. Chem. Soc.,* 105, 4835-4836 (1983).
Carroll et al., *J. Org. Chem.,* 55, 4426-4431 (1990).
Gellerman et al., *Tet. Lett.,* 33, 5577-5580 (1992).
Ali et al., *J. Chem. Soc., Chem. Commun.,* 1453-1454 (1992).
Partridge et al., *J. Chem. Soc. (C),* 632-635 (1962).
Tindale et al., *Aust. J. Chem.,* 37, 611-617 (1984).
Schäfer et al., *Angew. Chem. (Int. Ed.),* 10, 405-406 (1971).
Schäfer et al., *Angew. Chem. (Int. Ed.),* 10, 406-407 (1971).
Moody et al., *Tetrahedron,* 48, 3589-3602 (1992).
He et al., *J. Org. Chem.,* 56, 5369-5371 (1991).
Gellerman et al., *Tet. Lett.,* 34, 1823-1826 (1993).
Gellerman et al., *Tet. Lett.,* 34, 1827-1830 (1993).

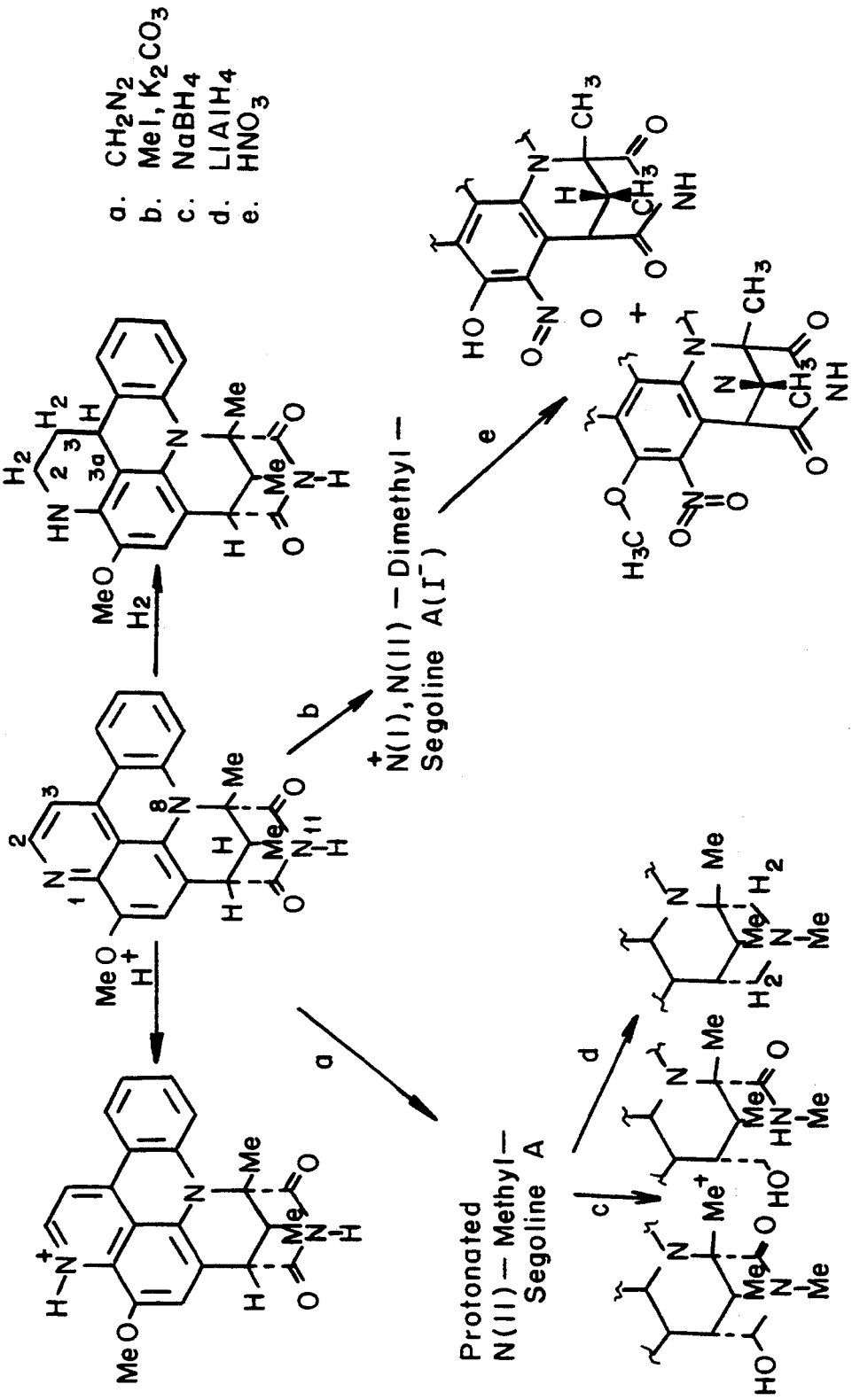
FIG. 2A Scheme I. Chemical Transformations of Segoline A

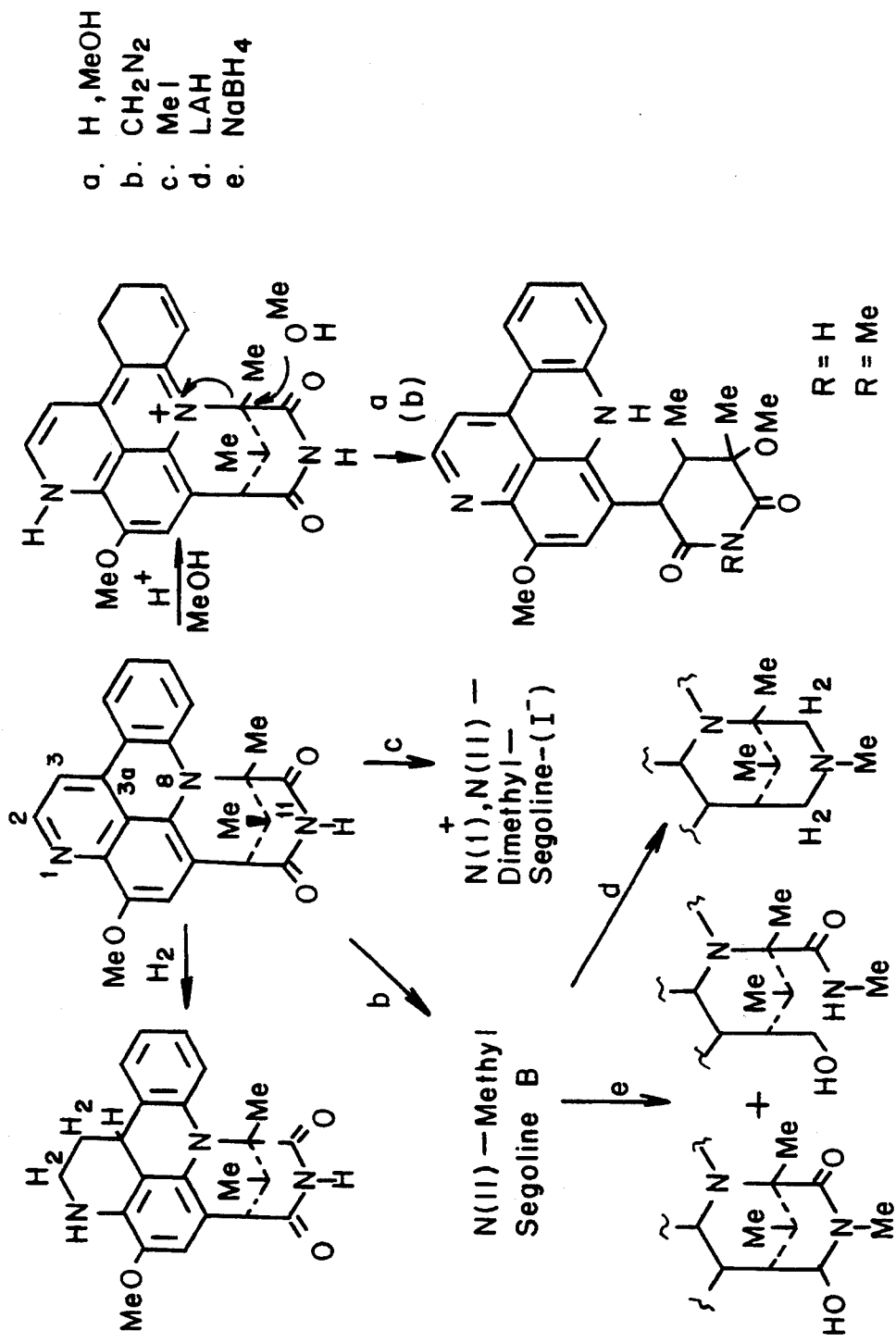

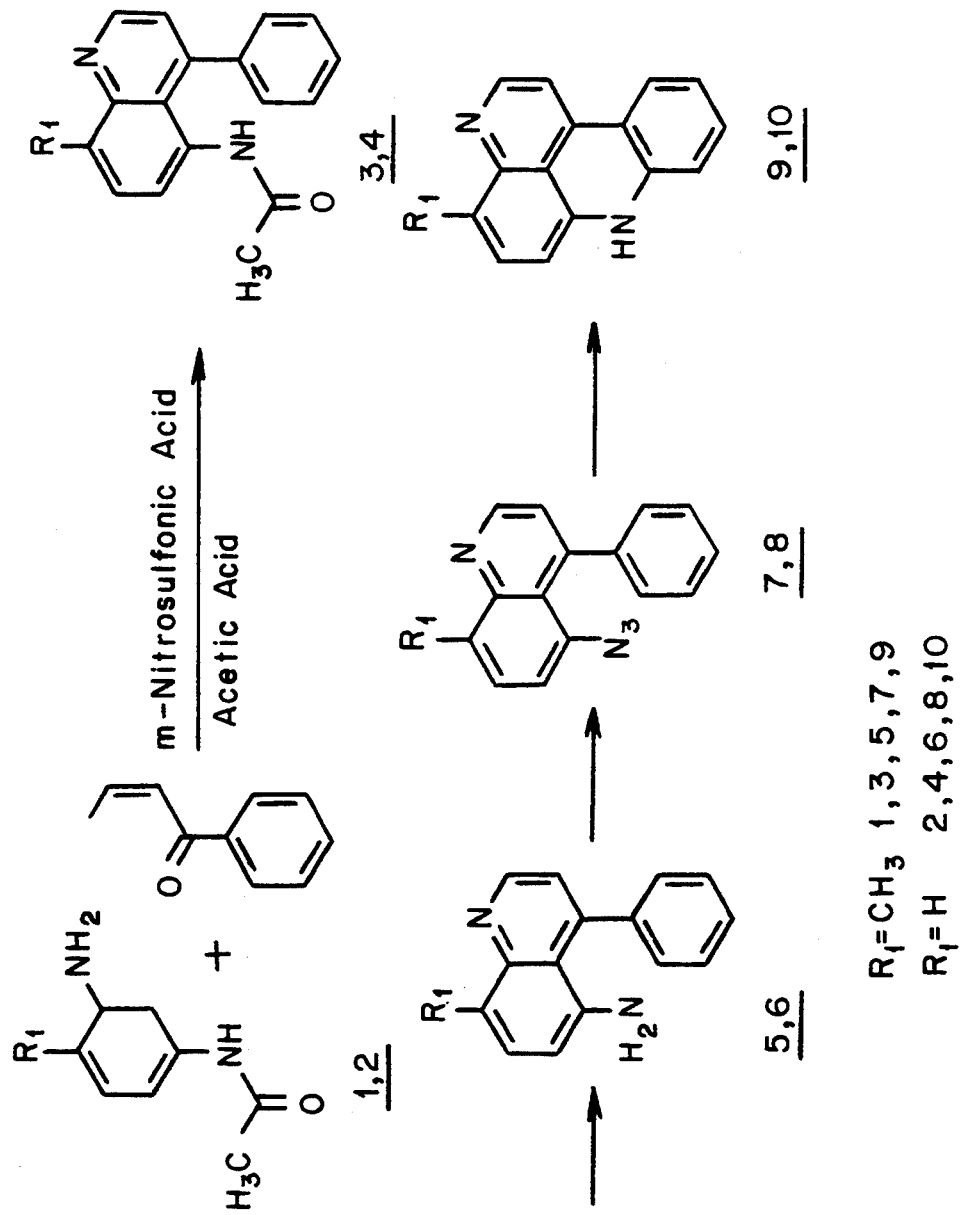

25

26

27

28

FIG. 7A a. aq. EtOH NaIO₃    b. HOAc, H⁺, m-NO₂PhSO₃Na

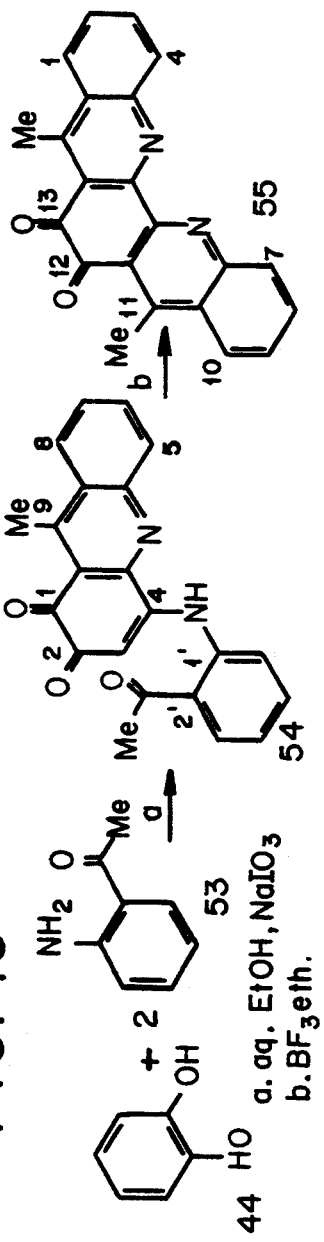
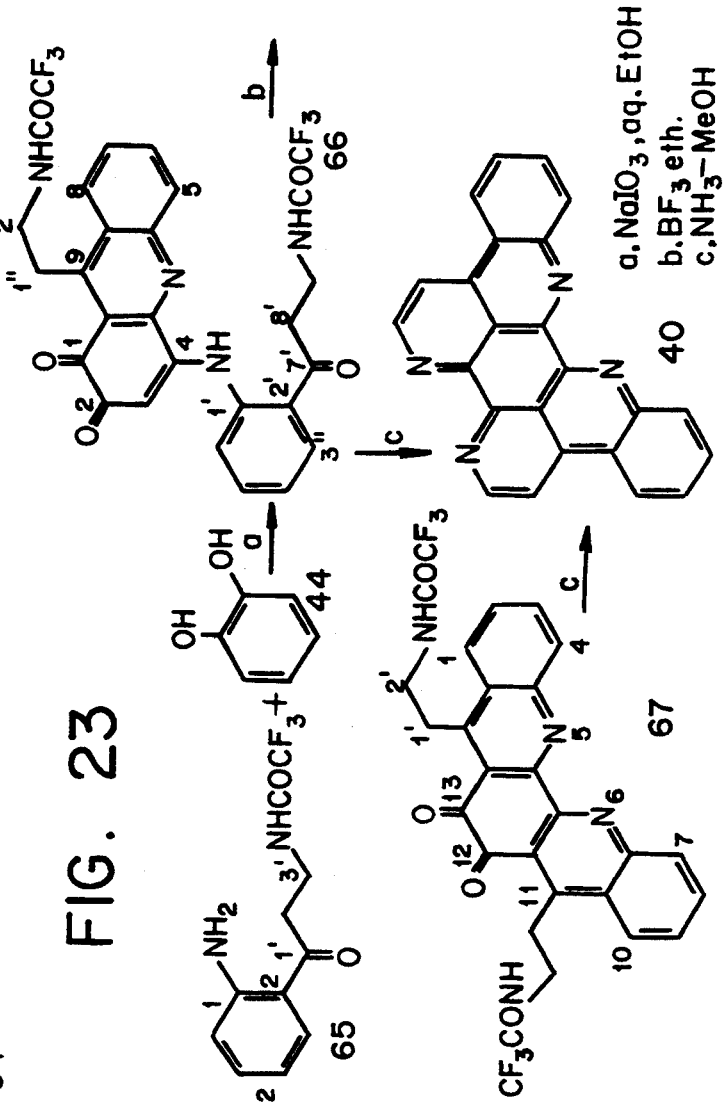
FIG. 19
FIG. 23

BIOLOGICAL APPLICATIONS OF ALKALOIDS DERIVED FROM THE TUNICATE EUDISTOMA SP.

This is a continuation-in-part of application Ser. No. 07/924,194 filed on Aug. 3, 1992, now U.S. Pat. No. 5,278,168.

BACKGROUND OF THE INVENTION

1. Field of the Invention

This invention relates to biological applications of alkaloids derived from the tunicate Eudistoma sp. and related compounds, to the preparation of synthetic pyridoacridines, and particularly to the synthesis of Eilatin.

2. Background of the Related Art.

In recent years it has become apparent that the sea offers an enormous biomedical potential. The marine environment is quite distinct from the terrestrial environment and a vast number of marine natural products with novel molecular architectures were already isolated and purified from diverse marine organisms. Surprisingly, only a small fraction of these novel compounds underwent detailed pharmacological and biological evaluations and only few of these were found to possess desirable biological and physiological activities, see Scheuer, "Marine Natural Products, Chemical and Biological Perspectives" *Academic Press*, New York, Vols. I-V, (1978-1983); Kaul et al., *Ann. Rev. Pharmacol.*, 26, 117-142 (1986); Scheuer, *Science*, 248, 173-177 (1990).

The inventors have been engaged in the last 10 years in a research endeavor that involves chemical, biochemical and cell biological studies of marine natural products derived from Red Sea organisms. This interconnected effort has already yielded what others have described as "perhaps the most stimulating compounds isolated from corals and sponges"—the latrunculins. See Kaul et al., *Ann. Rev. Pharmacol.*, 26, 117-142 (1986). The latrunculins, isolated from the Red Sea sponge, latrunculia magnifica react specifically with the actin-based cytoskeleton and appear to be the most powerful probes currently available for the pharmacological investigation of microfilament organization and function, See: Spector et al., *Science*, 214, 493-495 (1983); Coue et al., *FEBS Lett.*, 213, 316-318 (1987) and Spector et al., "Cell Motility and the Cytoskeleton", 13 127-144 (1989) Also see, U.S. Pat. No. 4,857,538 to Kashman et al. entitled New Compounds for the Study and Treatment of Microfiliment Organization in cells.

Recently, two of the co-inventors, Drs. Kashman and Rudi have isolated and purified six (6) new heterocyclic alkaloids from the purple tunicate Eudistoma sp. and have elucidated their structures, See Rudi et al., *Tetrahedron Lett.*, 29, 6655-6656 (1988); Rudi et al., *Tetrahedron Lett.*, 29, 3861-3862 (1988) and Rudi et al., *J. Org. Chem.*, 54, 5331-5337 (1989). The structures of these six (6) heterocyclic alkaloids (1) segoline A; (2) segoline B; (3) isosegoline A; (4) norsegoline; (5) Debromoshermilamine; and (6) Eilatin are shown in FIG. 1. The six (6) Eudistoma alkaloids have in common a fused tetracyclic benzo-3,6-diazaphenanthroline ring system that was first identified in the sponge metabolite amphimedine, see Schmitz et al., *J. Am. Chem. Soc.*, 105, 4835-4837 (1983) and more recently in some other polycyclic aromatic alkaloids isolated from unrelated marine organisms including sponges, tunicates (ascidians), and an anemone see for example, Cimino et al., *Tetrahedron*, 43, 4023-4024 (1987); Bloor et al., *J. Am. Chem. Soc.*, 109, 6134-6136 (1987); Cooray et al., *J. Org. Chem.*, 53, 4619-4620 (1988); Molinsky et al., *J. Org. Chem.*, 53, 1340-1341 (1988); Kobayashi et al., *J. Org. Chem.*, 53, 1800-1804 (1988); Kobayashi et al., *Tetrahedron Lett.*, 29, 1177-1180 (1988); Charyulu et al., *Tetrahedron Lett.*, 30, 4201-4202 (1989); Molinski et al., *J. Org. Chem.*, 54, 4256-4259 (1989); and, Schmitz et al., *J. Org. Chem.*, 56, 804-808 (1991); Gunawardana et al., *J. Am. Chem. Soc.*, 105, 4835 (1983); Carroll et al., *J. Or. Chem.*, 55, 4427 (1990); and He Hay-yh et al., *J. Org. Chem.*, 56, 5369 (1991).

Based on chemical structure, the Eudistoma alkaloids have been classified into 4 groups:

1. Three of the compounds display a high degree of structural similarity and were designated as Segoline A, segoline B, and Isosegoline A (segol means purple in Hebrew).
2. A fourth compound, lacks the imide moiety that is present in the above three compounds and was designated Norsegoline.
3. Another compound contains a thiazinone moiety. It was designated Debromoshermilamine A because it was found to be closely related to Shermilamine, a compound previously purified from a different tunicate tridideмnum sp. found in Pago Bay, Guam, as reported by Cooray et al., *J. Org. Chem.*, 23, 4619-4620 (1988).
4. The last compound was designated Eilatin (from tunicate collected in Eilat) is the most remarkable in having a rare, highly symmetrical heptacyclic structure.

In addition to these six (6) natural compounds, Drs. Kashman and Rudi have synthesized several derivatives of Segoline A as shown in Scheme I at FIG. 2(A), Segoline B as shown in Scheme II at FIG. 2(B); see, Rudi et al., *J. Org. Chem.*, 54, 5331-5337 (1989); also see, Gellerman, Rudi & Kashman, *Tet. Letters*, 33, 5577 (1992). Others have also attempted to synthesize similar compounds See, Ali et al., *J. Chem. Soc. Chem. Commun.*, 1453 (1992)

Chemically, the six (6) Eudistoma alkaloids appear to belong to a growing class of novel marine alkaloids that have in common a fused tetracyclic benzo-3,6-diazaphenanthroline ring system. There are scant reports concerning the biological activities of these related species indicating that many of them are cytotoxic to a variety of cancer cell lines see Cimino et al., *Tetrahedron*, 43, 4023 (1987); Bloor et al., *J. Am. Chem. Soc.*, 109, 6134 (1987); Molinski et al., *J. Org. Chem.*, 53, 1340 (1988); Kobayashi et al., *J. Org. Chem.*, 53, 1800 (1988); Kobayashi et al., *Tetrahedron Lett.*, 29, 1177 (1988); Charyulu et al., *Tetrahedron Lett.*, 30, 4201 (1989); Molinski et al., *J. Org. Chem.*, 54, 4256 (1989); Schmitz et al., *J. Org. Chem.*, 56, 804 (1991) but the mechanism by which they exert their cytotoxic effects is completely unknown.

At present it is not even clear whether all these novel marine alkaloids should be classed together, and whether they are produced by the source organism or by symbionts, see Rudi et al., *J. Org. Chem.*, 54, 5331-5337 (1989). The presence of six different alkaloids in the same Eudistoma sp organism is without precedent and provides a unique opportunity to shed some light on these problems.

SUMMARY OF THE INVENTION

The present invention discloses biological applications of synthetic and natural alkaloids derived from the tunicate Eudistoma sp. One aspect of the present invention is a for method regulating cell growth. The method comprises contacting one or more cells with an effective concentration of a compound for regulating cell growth. These compounds include:

Segoline A, Segoline B, Isosegoline A, Norosegoline, Debromoshermilamine, Eilatin, 4-methylpyrido[2,3,4-kl]acridine, pyrido[2,3,4-kl]acridine, 1-acetyl-2,6-dimethylpyrido[2,3,4-kl]acridine, a compound having the chemical structure:

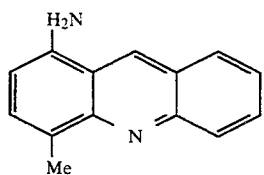

wherein $R_1$ is selected from time group consisting of phenyl, halogen, hydroxy, $CO_2$-Methyl, HO-Methyl, $COCH_3$, $CH_3$ and H; 12-demethyl carboxylate Norsegoline, Seco Eilatin, 4,7-dinitroeilatin, a compound laving the chemical structure:

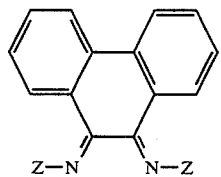

wherein Z is selected from the group consisting of phenyl, halogen, hydroxy, $CO_2$-Methyl, HO-Methyl, $COCH_3$, $CH_3$ and H; N(II)-methyl Segoline A, N(I)-dimethyl Segoline A(I−), N(II)-dimethyl Segoline A(I−), N(12)-methyl-Isogoline, N(1) -dimethyl-Norsegoline, N(8) -dimethyl Norsegoline, N(II)-methyl Segoline B, N(I) dimethyl Segoline B(I−), a compound having the chemical structure:

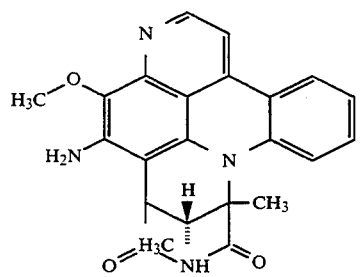

and a compound having the chemical structure of:

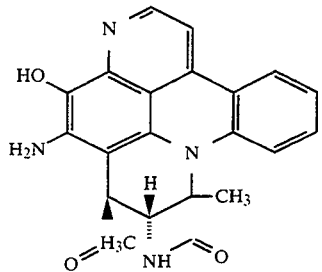

and a compound having the chemical structure of:

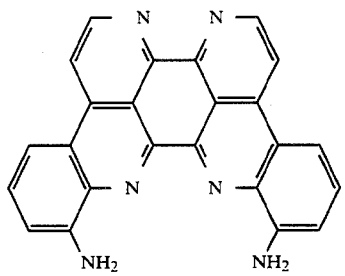

and derivatives and combinations of these compounds.

An effective concentration range for using these compounds can range from approximately 0.1 μM to 100 μM. The effective concentration range for a Eilatin, the most potent of these compounds, is from 0.01 μM to 0.99 μM, and the effective concentration range for the other compounds of the present invention is from about 1.0 μM to 100 μM. For the cells tested in the present invention the most effective concentration was shown to be:

(a) 12–52 μM for Segoline A, Segoline B and Isosegoline;
(b) 8–40 μM for Norosegoline;
(c) 6–32 μM for Debromoshermilamine;
(d) 0.05 to 0.5 μM for Eilatin;
(e) 7.5–12.5 μM for 4-methylpyrido[2,3,4-kl]acridine; and
(f) 2–5 μM for pyrido[2,3,4-kl]acridine.

The method of the present invention has been shown to suppress growth of tumor cells, and induced differentiation of the tumor cells. Additionally, the method has induced reverse transformation of the tumor cells.

In transformed cells, the method of the present invention has been shown to induce reverse transformation. The method of the present invention has been shown to inhibit the proliferation of cells. The examples show that the method of the present invention affects cyclic AMP mediated biological processes. The compounds of the present invention when used at their effective concentrations, affect the cyclic AMP mediated biological processes of the cells to achieve the results described above.

Another aspect of the present invention is the synthesis of a number of pyridoacridines and intermediates in the synthesis of these pyridoacridines. These compounds and their scheme for synthesis are illustrated in FIGS. 2C–2I. One compound according to the present invention has the chemical structure:

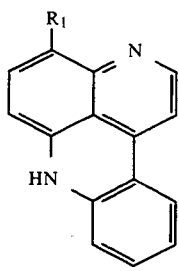

in which $R_1$ can include the following groups: phenyl, halogen, hydroxy, $CO_2$-Methyl, HO-Methyl, $COCH_3$, $CH_3$ and H. Preferred compounds include where $R_1$ is $CH_3$ or H.

Another compound according to the present invention has a chemical structure:

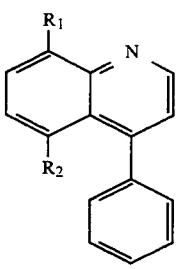

wherein $R_1$ can include the following groups: phenyl, halogen, hydroxy, $CO_3$-Methyl, HO-Methyl, $COCH_3$, $CH_3$ and H and $R_2$ can include the following groups: $NHOCH_3$, $NH_2$ and $N_3$; and preferably when $R_1$ is H or $CH_3$.

Another compound disclosed by the present invention 25 has the chemical structure:

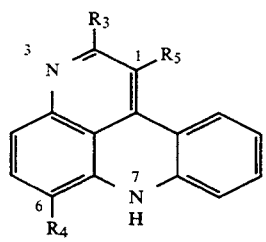

in which $R_3$, $R_4$, and $R_5$ can include the following groups: phenyl, halogen, hydroxy, $CO_2$-Methyl, HO-Methyl, $COCH_3$, H; and $CH_3$. Preferably in which $R_3$ and $R_5$ are $CH_3$, and $R_4$ is $COCH_3$.

Another compound according to the present invention has a chemical structure:

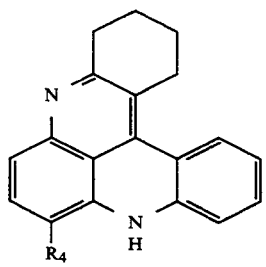

in which $R_4$ call include the following groups: penyl, halogen, hydroxy, $CO_2$-Methyl, HO-Methyl, $COCH_3$, of H, and $C_3$.

Another compound according to the present invention has a chemical structure:

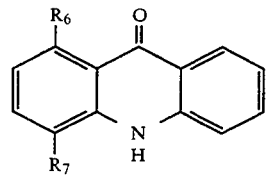

in which $R_6$ can include the following groups: $NHOCH_3$, $N_3$ and $NH_2$; and $R_7$ can include the groups: H, $CH_3$, phenyl, halogen, hydroxy, $CO_2$-Methyl, HO-Methyl, $COCH_3$.

Another compound according to the present invention has the chemical structure:

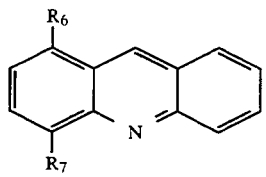

in which $R_6$ can include the following substituents: $NHOCH_3$, $N_3$ and $NH_2$; and $R_7$ can include: H, $CH_3$, phenyl, halogen, hydroxy, $CO_2$-Methyl, HO-Methyl, and $COCH_3$.

Another compound according to the present invention has the chemical structure:

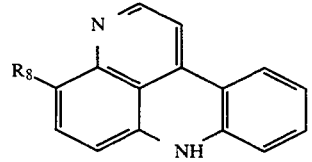

in which $R_8$ can include the following substituents: H, phenyl, halogen, hydroxy, $CO_2$-Methyl, HO-Methyl, $COCH_3$ and $OCH_3$; preferably $R_8$ is $OCH_3$.

Another compound according to the present invention has a chemical structure:

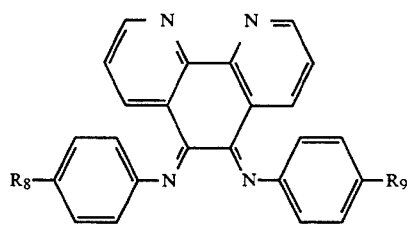

in which $R_8$ and $R_9$ can include the following substituents: H, $CH_3$ phenyl, halogen, hydroxy, $CO_2$-Methyl, HO-Methyl, $COCH_3$ and $OCH_3$; preferably where $R_8$ and $R^9$ are $OCH_3$ or H.

Other compounds according to the present invention are derivatives of Segoline A, and Eilatin, compounds 30, 32 and 34, respectively, as illustrated in FIG. 2I, and the intermediates leading to these compounds:

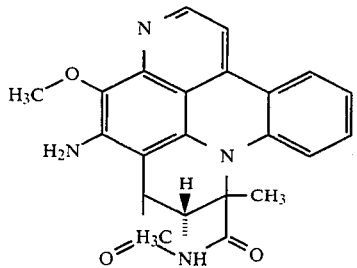

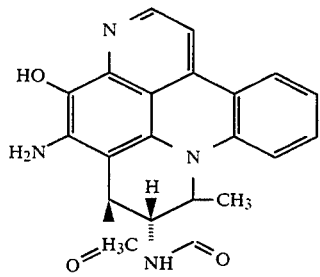

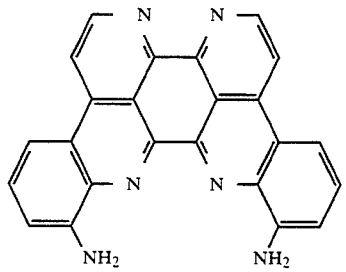

Other such derivatives may be prepared from each of the compounds described above and illustrated in FIGS. 1-2(A-I), in a similar manner as synthesized in the examples according to chemical methodologies well known to those skilled in the art.

Another aspect of the present invention is a process for synthesizing the compounds described above and the intermediate derived in synthesizing these compounds. The process includes the steps of:

(a) dissolving a compound having the chemical structure:

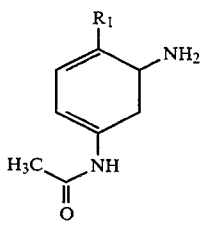

wherein $R_1$ is H or $CH_3$, in acetic acid with m-nitrosulfonic acid sodium salt at a temperature of about 65°–70° C.;

(b) adding vinylphenylketone to the solution of step (a) at a temperature of about 65°–70° C.;

(c) heating the reaction mixture of step (b) to a temperature of about 110° C.±5° C., or reacting in an ultrasonic bath at ambient temperature, for 1.5 hrs.±0.5 hrs.

(d) cooling the reaction mixture of step (c) to about 5° C.;

(e) contacting the reaction mixture of step (d) with ammoniacal ice, thereby forming a precipitate of a compound having the chemical structure:

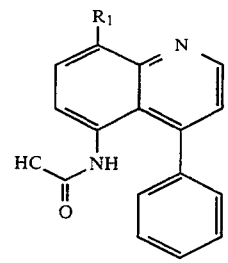

and, (f) separating the compound of step (e) from the mixture. The intermediate obtained in step (e) can then be used by:

(g) dissolving the intermediate obtained in step (e) in 80% sulfuric acid;

(h) heating the solution of step (g) to a temperature solution in an ultrasonic bath at ambient temperature, for about 1.5±0.5 hrs.;

(i) cooling the reaction mixture of step (h) to about 5° C.;

(j) contacting the reaction mixture of step (i) with ammoniacal ice;

(k) extracting the resulting amine with methylene chloride; and (l) evaporating the methylene chloride yielding the free amine compound having the chemical structure:

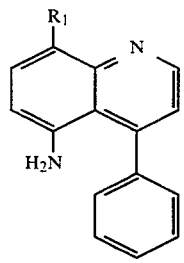

In the case where the $R_1$ substituent of the starting compound is H the process also includes the step of separating the compound obtained in step (e) from its isomer, preferably by flash silica gel chromatography utilizing $CHCl_3$—$CH_3OH$ as the eluant. The synthesis can continue from step (1) by:

(m) dissolving the amine compound in 1.5N HCl;

(n) cooling the solution of step (m) to about 0° C.;

(o) adding $NaNO_2$ to the solution of step (n);

(p) after about 20 minutes at about 0° C. adding NaN the solution of step (o);

(q) after about 10 minutes adding ammonia to pH 10 thereby obtaining a crude azide compound having the chemical structure:

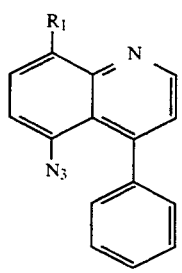

(r) extracting the crude azide with a solvent;
(s) evaporating the solvent thereby recovering the crude azide; and
(t) purifying the crude azide to yeild the pure azide compound. Preferably, in this process the solvent is methylene chloride and the purifying step is by silica gel chromotography. In continuing the synthesis from step (t), the process includes:
(u) dissolving the azide in durane under argon;
(v) heating the solution (u) to 200° C. for approximately 30 minutes;
(w) cooling (v) to about 5° C.;
(x) dissolving (w) in a suitable solvent;
(y) extracting 2NHCl a pyridoacridine compound having the chemical structure:

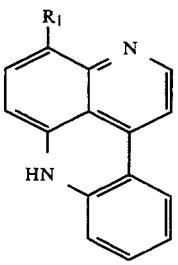

(z) neutralizing the acid with ammonia and extracting the resulting salt with a suitable solvent;
(aa) evaporating the solvent to recover the pyridoacridine ocmpound; and
(ab) purifying the resulting pyridoacridine compound. Preferably, the solvent of step (r) is $CH_2Cl_2$—$CH_3OH$ and purifying step (ab) is by silica gel chromatography.

Another process disclosed in the present invention is the synthesis including the steps of:
(a) combining a compound having the chemical structure

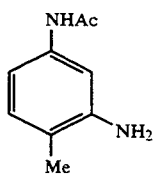

and
o-chlorobenzoic acid under Ullmann reaction conditions to afford a substituted dephenylamine;
(b) inducing cyclization of the pyridine ring of the substituted dephenylamine in the presence of poly phosphric acid (5 eq.) and at a temperature of 125° C.±5° C., or in an ultrasonic bath at ambient temperature, for about 1.5±0.5 hours; and;
(c) heating the reaction mixture obtained in step (b) a temperature of about 125° C.±5° C., or in an ultrasonic bath at ambient temperature, for about 1.5±½ hrs. in the presence of catalytic amounts of sulfuric acid ($H_2SO_4$) to yield a compound having time chemical structure:

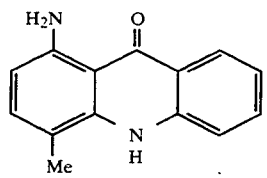

The synthesis can continue from the above intermediate as follows:
(d) reducing time compound obtained in step (c) with Na(Hg) to yield 1-amino-4-methylacridine. In addition, tire synthesis calm be continued by:
(e) heating said 1-amino-4-methylacridine with acetyl acetone and catalytic amounts of acid ($H_2SO_4$) in amyl alcohol at about a temperature of about 125°±5° C., or in an ultrasonic bath at ambient temperature, for about 1.5±0.5 hrs. thereby yielding 1-acetyl-2,6-dimethylpyrido-(2,3,4-kl)acridine. The 1-acetyl-2,6-dimethylpyrido (2,3,4-kl)acridine is then extracted from the reaction mixture.

The intermediate can be further processed as follows:
(g) reacting said 1-amino-4-methylacridine with cyclohexanone and catalytic amounts of acid ($H_2SO_4$) in amylalcohol at a temperature of about 125° C.±5° C. for 1.5±½ hrs. thereby yielding a compound having the chemical structure:

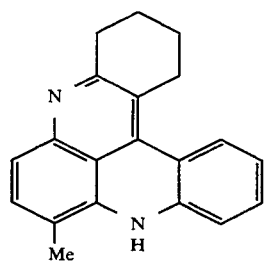

This compound can be further processed by:
(h) extracting the compound obtained ill step (g) from the reaction mixture.

If time starting materials, or intermediates of the above process are demethylated, i. e. do not conta in a methyl group, the process would finally yield 12-demethyl carboxylate Norsegoline.

Another process according to this invention is the synthesis according to the following steps:
(a) combining 1,8-phenathroline -5,6-dione in aniline or P-OMe-aniline (2.5 eq.) and in HOC (10 eq.),
(b) reacting the mixture under reflux conditions, or in an ultrasonic bath at ambient temperature, for about 1½±½ hrs. thereby yielding a compound having the chemical structure:

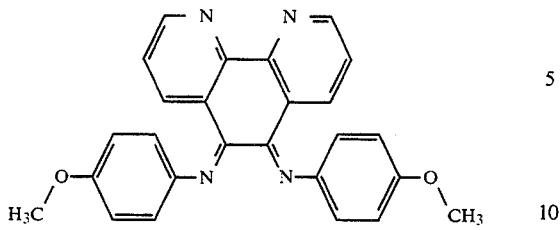

(c) extracting the compound obtained in step (b) from the reaction mixture; and (d) purifying the compound.

Another process for synthesis according to the present invention includes the following steps:

(a) combining 9,10-phenanthenequinone in aniline or P-OMe-aniline (2.5 eq.) and in HOC (10 eq.), (b) reacting the mixture under reflux conditions or in an ultrasonic bath at ambient temperature, for about $1\frac{1}{2} \pm \frac{1}{2}$ hrs. thereby yielding a compound having the chemical structure:

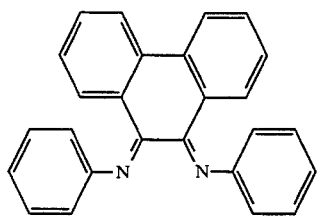

(c) extracting the compound obtained in step (b) from the reaction mixture; and (d) purifying the compound.

The compounds of the present invention can be modified in various ways, for example nitration of Segolina A & B yielding compounds 29 and 31, and of Eilatin yielding compound 33 can be carried out, followed by reduction of the resulting nitro groups to yield the corresponding amino compounds 30, 32 and 34. Eilatin has been demonstrated to afford Selectively the 4,7-dinitro derivative 33. Reduction of the nitro group yields the corresponding amino groups 34 from which a variety of derivatives are prepared (—OH, halogens, —CN, —CO$_2$H, etc.) via the diazonium ion. The regioselectivity of nitration (to C-14 in case of Segoline A and Segoline B, and C-4 and C-7 in case of Eilatin) has been demonstrated. Hydrogenation, with H$_2$, dithionite or Sn or Fe/HCl reduction of the nitro compounds affords the amino derivatives. The amines are further modified via diazonium salts (NaNO$_2$—HCl), and then changed into different groups using well established procedures for these compounds, (e.g. halogens, —CN) other nitration reagents, such as NO$_2$BF$_4$, HNO$_3$ -acetic acid, HNO$_2$—H$_2$SO at suitable reaction conditions are also used to achieve other substitutents. Many of the resulting new compounds are amenable to further chemical changes.

Another embodiment of the present invention includes a compound having the chemical structure:

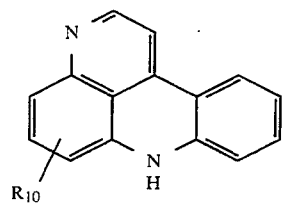

wherein $R_{10}$ is a substituent which can include a phenyl, halogen, hydroxy, CO$_2$-Methyl, COCH$_3$, CH$_3$, H, NHOCH$_3$, NO$_2$, NH$_2$, or N$_3$. In addition, the present invention includes compounds having the following chemical structures:

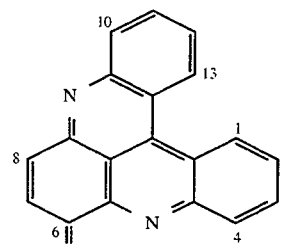

46

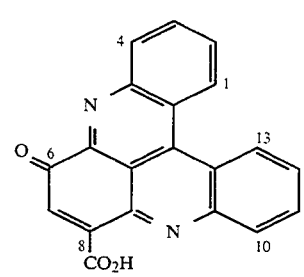

48

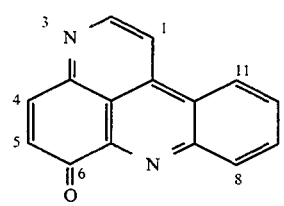

49

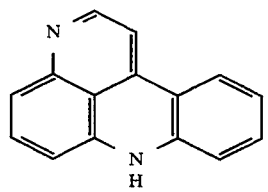

52

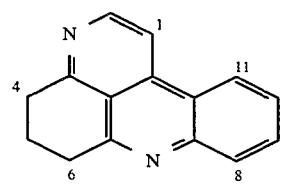

51

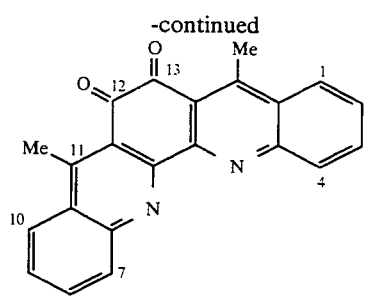

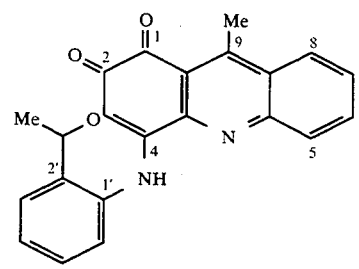

and derivatives thereof. Furthermore, the present invention includes a compound having the chemical structures selected from the group consisting of:

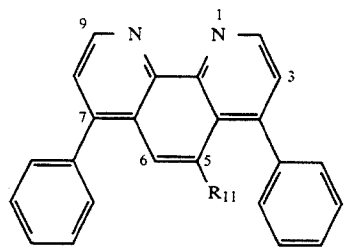

$R_{11} = NO_2$
$[R_{11} = N:]$

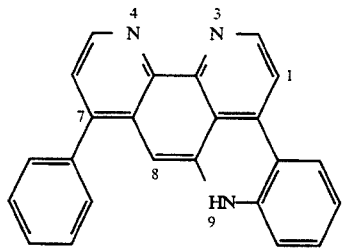

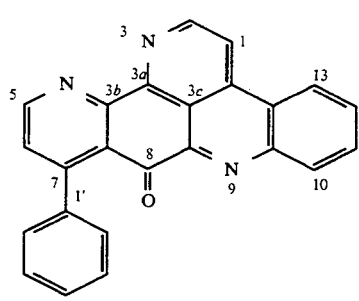

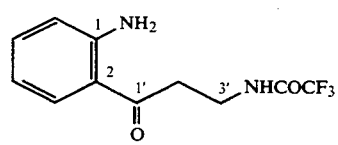

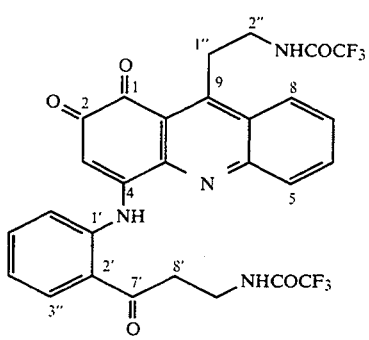

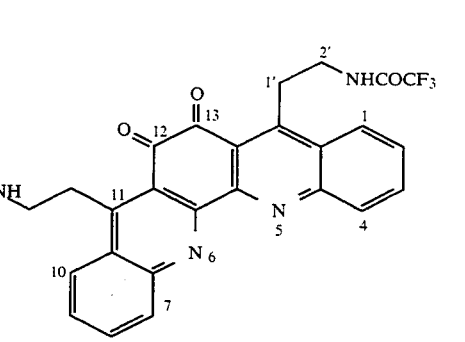

wherein $R_{11}$ is $NO_2$.

Another embodiment of the present invention includes a process for synthesizing, pyrido[k,l]acridine compounds, which includes the following steps:

Reacting a first compound which can include o-benzyquinone, hydroquinone, combinations and derivatives thereof, with a second compound which can include kynuramine, derivatives of kynuramine and combinations thereof, under appropriate reaction conditions, which preferably include mild oxidative conditions in aqueous EtOH and an oxidant which may include $NaIO_3$, $CeCL_3$ or $Fe(SO_4)_2$. The reaction thereby yielding a pyrido[k,l]acridine compound.

Another preferred process of the present invention is the synthesis of eilatin and its derivatives, which includes the following steps:

Reacting a first compound having the chemical structure:

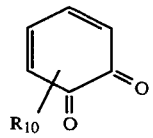

in which $R_{10}$ is a substituent which may include a phenyl, halogen, hydroxy, $CO_2$-Methyl, HO-Methyl, $COCH_3$, $CH_3$, H, $NHOCH_3$, $NO_2$, $NH_2$, or $N_3$. The first compound is reacted with a second compound in a 1:2 ratio, respectively. The second compound may include kynamurine having the chemical structure:

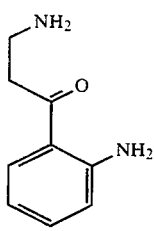

or derivatives of kynamurine and combinations thereof under appropriate, mild oxidative reaction conditions.

In this process, a preferred intermediate is a 1,10-phenathroline-5,6-dione derivative, which is further preferably treated with a mild base, preferably with $NH_3$—NaOH, to yield eilatin having the chemical structure:

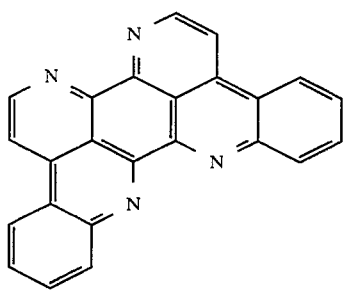

For a better understanding of the present invention, reference is made to the following description and examples, taken in conjunction with the accompanying tables, the scope of which is pointed out in the appended claims.

BRIEF DESCRIPTION OF THE DRAWINGS

FIG. 2(A) shows Scheme I, the chemical transformation of Segoline A(1);

FIG. 2(B) shows Scheme II, the chemical transformation of Segoline B(2);

FIG. 2(C) shows Scheme III, the steps for synthesizing compound 9, 4-methylpyrido[2,3,4-kl]acridine, and compound 10, pyrido[2,3,4-kl]acridine;

FIG. 4 is a series of phase-contrast micrographs showing the long-term effects of the adenylyl cyclase activator, forskolin and the Eudistoma alkaloids on morphological appearance of N1E-115 cells. A,B: Untreated cells 3 (A) and 6 (B) days after subculture. C,D: Cells grown for 3 (C) and 6 (D) days with 50 μM forskolin. E,F: Cells grown for 3 (E) and 6 (F) days with 39 μM Segoline A. G,H: Cells grown for 3 (G) and 6 (H) days with 0.14 μM Eilatin.

FIG. 19 shows the synthesis of 1:2 addicts, compounds 54 and 55 as potential precursors of eilatin.

FIG. 23 shows the preferred two step, and three step biomemetic total synthesis of eilatin carried out in Example VIII.

DETAILED DESCRIPTION OF THE INVENTION

Evaluation of the biological effects of the six Eudistoma alkaloids and two of the synthetic pyridoacridines, 4-methylpyrido[2,3,4-kl]acridine and pyrido[2,3,4-kl]acridine revealed that all eight compounds possess potent growth regulatory properties (see Example V). A single application of the Eudistoma alkaloids or synthetic pyridoacridines inhibited cell division in normal and cancer cell lines and induced differentiation in neuroblastoma cells and reverse transformation in virus-transformed fibroblast cells. Biochemical studies further showed that the alkaloids mimic the short-term effects of cAMP analogues on cellular processes that are known to be mediated by cAMP (see Example VI). These results suggest that the growth regulatory properties of the Eudistoma alkaloids are mediated by cAMP. However, in marked contrast to the permanent effects induced by a single application of the Eudistoma alkaloids, a single application of cAMP analogues or agents that elevate cytosolic cAMP levels did not sustain growth inhibition. The cells resumed division within 48 h after drug application and became confluent after a week. These results strongly suggest that the Eudistoma alkaloids exert their growth regulatory effects via a unique and novel action on the cAMP signaling system.

Figure 1:
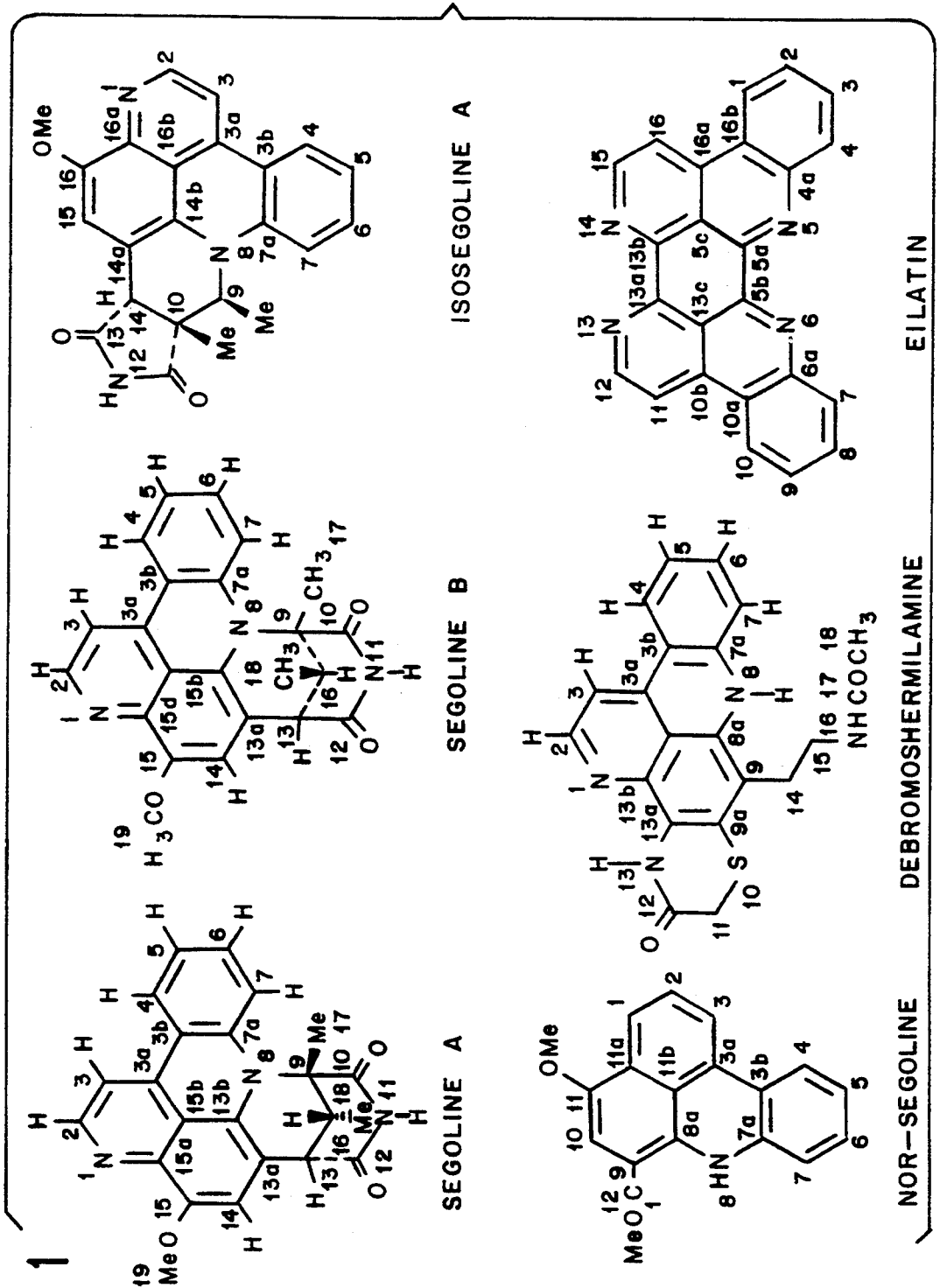
FIG. 1 shows the structure of Eudistoma alkaloids, Segoline A Segoline B, Isosegoline A, Norsegoline, Debromoshermilamine and Eilatin.

FIG. 1 shows the structure of six Endistoma alkaloids. Segoline A; Segoline B; Isosegoline A; Norsegoline; Debromoshermilamine; and Eilatin. FIG. 2 (A) shows Scheme I, the chemical transformation of Segoline A(1); FIG. 2 (B) shows Scheme II, the chemical transformation of segoline B(2); FIG. 2 (C), Scheme III shows the structure of synthetic pyridoacridine (9) 4-methylpyrido[2,3,4-kl]acridine; and FIG. 2(D), Scheme IV shows the structure of synthetic pyridoacridine (10) pyrido[2,3,4-kl]acridine.

The inventors have surprisingly discovered that a one time exposure of a cloned cell line isolated from the C-1300 mouse neuroblastoma tumor to any one of the eight (8) compounds completely inhibited cell proliferation and induced a process of differentiation during which the cells extended long neurites and developed other characteristic neuronal properties (FIGS. 3–5). Likewise, fibroblast cells transformed by hamster sarcoma virus (HSV) which display altered growth patterns and aberrant morphologies responded to a one time exposure of the Eudistoma alkaloids (FIGS. 8,9) and of the two synthetic pyridoacridines (FIG. 10) by restoration of normal cell growth and morphology, a phenomenon known as "reverse transformation" that is described by Lockwood et al., J. Cell. Biochem., 33, 237–255 (1987). FIGS. 6 and 7 show that in normal fibroblasts each of the eight (8) compounds slowed down cell division and caused cell flattening or elongation that resulted in lower saturation densities. It should be noted, however, that there are quantitative as well as qualitative differences among the four groups of the Eudistoma alkaloids and between the six (6) natural compounds and the two (2) synthetic pyridoacridines with regard to their actions at the cellular level. For example, Eilatin, which has an unusually symmetrical heptacyclic structure, was found to be 100 times more potent than the other five (5) naturally occurring compounds, as well as the synthetic pyridoacridines, and more cytotoxic to transformed cells than to normal cells (See example V).

The effects of the Eudistoma alkaloids and the two synthetic pyridoacridines on normal fibroblasts are strikingly similar to those obtained by chronic treatment with cAMP analogues or agents that elevate cAMP. In addition, many of the reagents and growth conditions that regulate growth and differentiation of transformed cells do so by elevating intracellular cAMP levels as reported by Lockwood et al, J. Cell. Biochem., 33, 237–255 (1987); Willingham, Int. Rev. Cytol., 44, 319–363 (1976); Schubert, "Developmental Biology of cultured Nerve, Muscle, and Glia", John Wiley & Sons, New York (1984). Accordingly, the inventors carried out the foregoing experiments to determine whether the Eudistoma alkaloids exert their growth regulatory effects via the cAMP signaling system. At the cell biological level the action of the Eudistoma alkaloids were compared to the action of several cAMP analogues and agents that elevate intracellular cAMP levels. These include the adenylyl cyclase activator forskolin, the phosphodiesterase inhibitors theophylline and IBMX, the cAMP analogues dibutyryl cAMP (dbcAMP), 8-(4-chlorophrnylthio) cyclic AMP (CPT-cAMP) and 8-chloro-cAMP. The results of these experiments are presented in FIGS. 4–8, 10 and show that the short-term effects of the Eudistoma alkaloids resemble those of the cAMP elevating agents. However, in marked contrast to these agents whose effects begin to wane within 48 hours after drug addition, it took only a single exposure of the normal or the transformed cells to the Eudistoma alkaloids to inhibit cell proliferation and to induce and sustain what appears to be permanent differentiation in neuroblastoma cells and reverse transformation in the virus transformed fibroblast cells.

Particularly significant is the comparison with the two cAMP analogues CPT-cAMP and 8-chloro-cAMP. These site-selective cAMP analogues which bind preferentially to type II cAMP-dependent protein kinase were shown to be powerful regulators of growth and differentiation of cancer cell lines and are considered as new possible tools in the treatment of cancer as reported by Katsaros et al., *FEBS Lett.* 223, 97–103 (1987), Tagliaferri et al. *Cancer Res.* 48, 1642–1650 (1988), and Tortora et al., *Proc. Natl. Acad. Sci. USA* 87, 705–708 (1990). The results described in these Examples indicate that the Eudistoma alkaloids and the synthetic pyridoacridines may affect target proteins that are associated with activation of type II rather than type I cAMP-dependent protein kinase and that their pharmacological properties are more desirable than those of the site-selective cAMP analogues.

At the biochemical level, the inventors assessed the action of several of the Eudistoma alkaloids, and the two synthetic pyridoacridines, on two well characterized short-term cAMP-mediated cellular processes involved in hepatic glucose metabolism, as well as on release of growth hormone from anterior pituitary cells. The cAMP-mediated processes involved in hepatic glucose metabolism include inhibition of pyruvate kinase (PK) activity and induction of mRNA for P-enolpyruvate carboxykinase (PEPCK). PK is a key glycolytic enzyme whose activity is inhibited by cAMP-dependent phosphorylation, whereas PEPCK is a key enzyme in the gluconeogenesis pathway whose gene transcription rate is stimulated by cAMP, see Pilkis et al., *Annu. Rev. Nutr.*, 11, 465–515 (1991); Maghrabi et al., *J. Biol. Chem.*, 257, 233 (1982); Hod et al., *J. Biol. Chem.* 259, 15603–15608 (1984); Granner et al., *J. Biol. Chem.*, 265, 10173–10176 (1990). Growth hormone is a major product of anterior pituitary cells whose release is regulated by cAMP, see Bilezikjian et al., *Endocrinology*, 113, 1726–1731 (1983); Ray et al., *Endocrinology* 45, 175–182 (1986); Gabriel et al., *Neuroendocrinology*, 50, 170–176 (1989). The inventors have found that the Eudistoma alkaloids, like cAMP analogues, inhibit PK activity and stimulate PEPCK mRNA accumulation, as well as growth hormone release (FIGS. 11-13) suggesting that the growth regulatory effects of the Eudistoma alkaloids are mediated by the cAMP signaling system.

Major Implications of The Present Invention

1. By using a cell line isolated from the C-1300 mouse neuroblastoma tumor and virus transformed fibroblast cells the inventors have found that the Eudistoma alkaloids and the two synthetic pyridoacridines regulate cellular growth and differentiation of cancer cell lines. Furthermore, by using the normal counterpart of the transformed fibroblast cell line, the inventors found that the effects of the alkaloids on normal cells are similar to those of cAMP analogues or agents that elevate cAMP. Normal cells, however, are less sensitive to these alkaloids and in particular to the most potent compound, Eilatin. In fact, Eilatin has no effect on normal cells at concentrations that induce differentiation and reverse transformation of transformed cells.

The cell culture systems described above are highly suitable for studying the effects of novel drugs on the regulation of cellular growth and differentiation. Neuroblastoma cell lines have been used extensively as a model of nerve cell differentiation because various agents and treatments which inhibit cell proliferation cause neuroblastoma cells to undergo a controlled process of differentiation during which they extend long neurites and develop other characteristic neuronal properties; for example see: Schubert, "Developmental Biology of cultured Nerve, Muscle, and Glia", John Wiley & Sons, New York (1984). Likewise, many virus-transformed cells which display altered growth patterns and aberrant morphologies can respond to various agents, primarily those that elevate intracellular cAMP levels, by restoration of normal cell growth and morphology, a phenomenon known as "reverse transformation", as described by Lockwood et al., *J. Cell. Biochem.* 33 237–255 (1987). Finally, the concomitant use of normal fibroblast cells is highly significant in better characterizing the biological effects of novel drugs and their relationship to other compounds with known biological actions. Moreover, the use of normal cells helps to determine whether a given compound is simply cytotoxic, and indiscriminately affects normal and transformed cells, or whether the compound possess desirable pharmacological properties that can be further exploited in developing new drugs.

2. Another important implication of the present invention concerns the findings that the Eudistoma alkaloids may act on the cAMP signaling system. When compared to other drugs that are currently available to probe the cAMP system, or for that matter the other signal transduction systems that are involved in growth regulation of cancer cells, the Eudistoma alkaloids have a unique mode of action. This aspect of the present invention potentially opens new avenues in the ever expanding field of cAMP research and in the development of new drugs to characterize and correct perturbations of this ubiquitous central regulatory system, and in particular perturbations in normal cell growth and differentiation that lead to cancer.

The cAMP system functions to coordinate and regulate diverse cellular processes ranging from breakdown of glycogen in liver cells, to regulation of growth and differentiation, see Stryer, "Biochemistry" Ch. 38, W. H. Freeman & Co, New York (1988); Alberts et al., "Molecular Biology of the Cell"2d ed., CH. 12, Garland Publishing, New York (1989); Willingham, (1976) supra; Schubert, (1984) supra; and Tortora, et al., *Proc. Natl. Acad. Sci. USA*, 87 705–708 (1990). Perturbations of this system are responsible for many disease states, and may underlie oncogenic transformation of normal cells, as discussed by Lockwood et al., (1987) supra. Although cyclic AMP is considered to be the most important regulatory molecule in mammalian cells, the mechanisms by which it exerts its diverse effects are far from being understood. This is due to the complex multistep and pleitropic process by which binding of hormones to plasma membrane receptors stimulate the membrane bound enzyme adenylyl cyclase which catalyzes cAMP synthesis. Cyclic AMP in turn activates the cAMP-dependent protein kinases which cause a cascade of protein phosphorylations, and simultaneously alters numerous steps in many metabolic pathways. Termination of hormonal action is achieved by cyclic nucleotide phosphodiesterases enzymes which degrade cAMP, and by phosphoprotein phosphatases, enzymes which dephosphorylate the target proteins. These features makes the study of the cAMP system difficult and present a major challenge for present day molecular and cell biologists.

A fundamental approach to investigate the cyclic AMP-mediated cellular processes and their perturbations is to use specific drugs that will react with one of the steps or the components involved in the cAMP-induced regulatory cascade and will affect cell behavior, as described by Stryer "Biochemistry" W. H. Freeman & Co. New York, Ch. 38 (1988). Thus, most of the information concerning the involvement of the cAMP signaling system in cellular activities relied on the use of drugs that increase cytosolic cAMP levels, or mimic its action. These include the adenylyl cyclase activator, forskolin, various methylxanthines that inhibit cAMP phosphodiesterases, and permeant cAMP analogues. The thirst for drugs that affect the cAMP system is manifest by the fact that since its discovery in 1981 as a result of a Hoeschst program designed to screen plant extracts in India for cardiovascular and other pharmacological activities, forskolin rapidly has become the most extensively used drug in cAMP research, as discussed by Seamon et al., *Advances in Cyclic Nucleotide and protein phosphorylation Res.*, 20 1–150 (1986) and is discussed in more than 500 publications per year. The inventors' findings that the Eudistoma alkaloids and the two synthetic pyridoacridines exert a novel action on the cAMP system and are more powerful than any of the drugs that are currently available to probe this system is a major contribution to the ever expanding field of cAMP research.

3. Finally, the inventors' discovery that the Eudistoma alkaloids and synthetic pyridoacridines regulate growth and promote differentiation of transformed cells is highly significant in the continuous search for better ways of restraining the uncontrolled proliferation of cancer cells. The fact that similar compounds were found in different organisms in different geographic locations may indicate an important new family of marine metabolites that regulate cell growth and differentiation. Normal cell division is a highly regulated process that is governed by a complex set of controls, so that each stem cell generates one daughter stem cell and one cell that is committed to terminal differentiation after a strictly limited number of division cycles. The two types of aberration that can give rise to the unrestrained proliferation characteristic of cancer involve either a failure of stem cells to produce a non-stem-cell daughter, or a failure of daughter cells to differentiate normally, Alberts et al., "Molecular Biology Of The Cell", Garland Publishing New York, 2d ed., Ch. 21, (1989). Mutations or epigenetic changes that block the normal maturation of cells are presumed to play a critical role in many cancers. For example, neuroblastoma and several forms of leukemia seem to arise from a disruption of the normal program of differentiation, so that the committed nerve or blood cell continues to divide indefinitely instead of terminally differentiating. This is why in the treatment of cancer, drugs that promote cell differentiation like the Eudistoma alkaloids can be very valuable therapeutic tools in what is known as "differentiation therapy" and may be as important as currently used drugs that simply kill dividing cells.

Accordingly, the results obtained in the foregoing Examples clearly show that the Eudistoma alkaloids and the synthetic pyridoacridines represent a new class of powerful agents that regulate cellular growth and differentiation. These results support the contention that these compounds act on the cAMP signaling system in a unique and novel way. They may, therefore, have enormous potential as a new tool for cAMP research, as new drugs in cancer treatment, and in other treatments affecting perturbations of the CAMP system.

EXAMPLES

Example I

Chemical Isolation and Purification

During the course of scuba diving expeditions to survey the constituents of tunicates in the Red Sea, the inventors collected samples of the purple tunicate Eudistoma sp. from various locations in the Gulf of Eilat, Straits of Tiran, and Gulf of Suez. The samples were deep-frozen immediately after collection, freeze-dried, and then extracted with methanol:chloroform (2:8) solution to yield ca. 2 g extract from 100 g of dry tunicate. The crude extract was separated by chromatography on a silica gel column and eluted with chloroform-hexane (7:3), chloroform, and chloroform with increasing amounts of methanol up to 15%. Repeated chromatographies on silica gel yielded six (6) compounds. Three additional compounds were detected but in minuscule amounts that did not allow structural determination.

Example II

Structural elucidation of the six Eudistoma alkaloids

FIG. 1 shows the structures of the six Eudistoma alkaloids, Segoline A; Segoline B; Isosegoline A; Norsegoline; Debromoshermilamine; and Eilatin, which are characterized as follows:

Segaline A ($C_{23}H_{19}N_3O_3$, m/e 385). The most prevalent compound was isolated in ca. 0.4% dry weight. Intensive 1D and 2D NMR studies, including Homonuclear correlation spectroscopy (COSY), difference nuclear Overhauser effects (d-NOE), short- and long-range CH-correlations, correlation spectroscopy via long-range coupling (COLOC) and heteronuclear COSY (HETCOSY) experiments, led to the structural determination of the aromatic portion of the molecule and of several aliphatic moieties. However, the large number of long-range CH- correlations interfered with the unraveling of the precise structure. This was resolved by a single-crystal X-ray analysis. Segoline A was found to be an alkaloid with a new skeleton. It embodies a tetracyclic aromatic ring system similar to that of several marine alkaloids reported recently Schmitz et al., *J. Org. Chem.* 56 804–808 (1991) but the aliphatic site and its combination with the heterocycle are altogether new.

Segoline B ($C_{23}H_{19}N_3O_3$, m/e 385). Isolated in ca. 0.1% dry weight, its structure was found to be closely related to that of segoline A, as evidenced by the almost identical NMR data for the great part of the two molecules. The major differences between the NMR data of compounds 1 and 2 were in the alicyclic portion of the molecule, suggesting that compound 2 is a diastereomer of compound 1. By measuring the CD Cotton effects, it was concluded that Segoline B differs from Segoline A in the chirality of C-16.

Isosegoline A ($C_{23}H_{19}N_3O_3$, m/e 385). Another more polar isomer was isolated in ca. 0.01% dry weight. The NMR data suggested the same tri-substituted benzo-3,6-diazaphenanthroline ring system as in segoline A and segoline B, but a different imide moiety. From the NMR studies and the chemical behavior of the molecule it was concluded that the glutarimide ring of segoline A and segoline B is replaced in Isosegoline A by a succinimide. The absolute configuration of Isosegoline A was related to that of Segoline A on the basis of similar CD Cotton effects.

Norsegoline ($C_{18}H_{14}N_2O_3$, m/e 306). A less polar compound of a different molecular formula was obtained in minute amounts (ca. 0.001% dry weight). From the NMR data it was evident that norsegoline contains the same benzodiazaphenanthroline heterocycle as in compounds 1–3, but lacks the other rings. Instead, the spectroscopic data proposed a carbomethoxy moiety and another methoxy group, the location of which were established mainly by COSY and d-NOE experiments.

Debromoshermilamine ($CS_{21}H_{18}N_4O_2S$, m/e 390). Several of the collections of the Eudistoma sp. resulted in small amounts of compound 5 (ca. 0.05% dry weight). Intensive NMR work revealed this compound to be very similar to Shermilamine A which was isolated from the purple tunicate Trididemnum sp. collected in Pago Bay, Guam by Scheuer's group, Cooray et al., *J. Org. Chem.*, 53, 4619–4620 (1988). The only differences between the two compounds is the absence of the bromine in compound 5 which must, therefore, be 6-Debromoshermilamine A. More recently, Scheuer's group reported the isolation from the same tunicate of the debromo- compound which they designated as Shermilamine B Carroll et al., *J. Org. Chem.*, 54, 4231–4232 (1989).

Eilatin ($C_{24}H_{12}N_4$, m/e 356). The sixth compound was isolated in minute amounts (ca. 0.001% dry weight) from a collection in Eilat, hence the name. The molecular formula revealed 21 degrees of unsaturation suggesting a polyheterocyclic system. The high symmetry of the molecule and the overlapping signals in the NMR spectrum hampered an unequivocal determination of the structure of the molecule. The structure was finally determined by a single-crystal X-ray analysis and the complete NMR line assignment was then carried out. Eilatin was found to possess a completely new, highly symmetrical, seven membered ring system.

Example III

Derivatization and Chemical Transformation

As a first step towards a structure-activity study, we have prepared 19 derivatives. Eight Segoline A derivatives were prepared, as shown in Scheme I, FIG. 2(A). The nitration (leading to an important intermediate), of the anisole ring was clear from the disappearance of the singlet at d 7.47s and in compound 22 of the OMe too. Eight derivatives of Segoline B were prepared as shown in Scheme II, FIG. 2(B). N(12)-methyl-Isosegoline was prepared using diazomethane, N(1),N(8)-dimethyl-norsegoline was prepared using $CH_3I$, and 4,7-dinitroeilatin was synthesized by nitration of Eilatin (Disappearance of the doublet at $\delta=8.70d(J=8)$, and shift of H-3 to $\delta=8.78$; the other peaks are $\delta=9.29d(J=5.7)$, $8.50d(J=5.7)$, $8.23dd(J=7.9,1.2)$, $7.90t(7.9)$.

Example IV

Synthesis of Pyridoacridines, (Compounds 9 & 10)

The synthesis of compounds 2–10 is illustrated in Scheme III, FIG. 2(c).

I. Synthesis of 4-methyl pyrido[2,3,4-kl]acridine (9, $R_1=Me$)

Synthesis of Compound 3

Compound 1 described by Schatten, Org. Syn., 11, 32 (1931), (0.5 g) was dissolved in acetic acid (30 ml) with m-nitrosulfonic acid sodium salt (1 g) at 65°–70° C. Vinylphenylketone (0.45 g) was added dropwise at 65°–70° C. After 15 min the temperature was raised to 110° C. and kept at this temp. for 1.5 hrs. After cooling the reaction mixture was poured on ice cold ammonia and the precipitate 3 filtered under vacuum. (h=25%). [Skraup reaction].

Synthesis of Compound 5

Acetamide 3 (200 mg) was dissolved in 80% sulfuric acid (5 ml) and warmed to 130° C. for 2 hrs. The cooled solution was poured over ammoniacal ice and the resulting amine 5 extracted with methylene chloride. Evaporation of the $CH_2Cl_2$ gave the free amine 5 as an oil. (h=70%).

Synthesis of 7

Compound 5 (400 mg) was dissolved in 1.5N HCl (5 ml) then cooled down to 0° C. $NaNO_2$ (150 mg) was added, and after 20 min. at 0° C., $NaN_3$ (150 mg) was added. 10 min. later ammonia was added to pH=10 and the resulting azide extracted with $CH_2Cl_2$ (3×50 ml). Evaporation of the $CH_2Cl_2$ yielded the crude azide 7 as dark red oil which was purified by silica gel chromatogrphy to yield 160 mg.

Synthesis of Compound 9

As illustrated in Scheme III, FIG. 2(C) Azide 7 (200 mg) was dissolved in durane (5 ml) under argon and slowly warmed up to 200° C. (30 min). The cooled reaction mixture was dissolved in $CH_2Cl_2$ (50 ml) and 9 extracted with 2N HCl (3×20 ml). The acid was then basified with ammonia and extracted with $CH_2Cl_2$-MeOH (95:5, 3×30 ml). Evaporation followed by silica gel chromatography yielded compound 9 (100 mg).

Compound 3 Amorphous powder, m.p. 214° (acetone), $C_{18}H_{16}N_2O$ (m/z 276), $n_{max}$: 1645, 1600, 1510, 1380, 1010, 950 cm$^{-1}$. $d_H$ (CDCl$_3$): 8.86d (J=4.2), 7.72d(J=7.7), 7.35d(J=7.7), 7.48m, 7.32m(5H), 7.16d(J=4.2), 6.84brs (NH), 2.81s (Me), 1.45s(Me). $d_c$(CDCl$_3$): 169.5, 156.1, 147.6, 144.1, 140.6, 138.7, 135.2, 127.2, 126.9, 126.5, 124.3, 120.6, 112.2, 24.3, 19.1.

Compound 5 Amorphous powder, $C_{16}H_{14}N_2$ (m/z 234). $d_H$(CDCl$_3$): 8.74d (J=4.3 Hz), 7.27m(6H), 6.96d(J=7.6), 2.62s (Me). $d_c$(CDCl$_3$): 154.0, 143.2, 142.7, 140.8, 136.7, 135.1, 131.7, 126.6, 126.4, 125.9, 123.8, 119.3, 114.2, 22.9s (Me).

Compound 7 Red oil, $C_{16}H_{12}N_4$ (m/z 232, M-N$_2$), $n_{max}$ 2210, 1620, 1600, 1450, 1310, 1210 cm$^{-1}$. $d_H$(CDCl$_3$): 8.91d, (4.4 Hz), 7.60d(J=7.8), 7.15m(7H) 2.82s(Me). $d_c$(CDCl$_3$): 157.2, 148.1, 146.2, 141.7, 139.6, 136.6, 136.3, 126.1., 125.7, 124.9, 121.4, 119.6, 114.9, 23.8(Me).

Compound 9 Amorphous powder, mp>300° C. $C_{16}H_{12}N_2$ (msci, m/z 233, MH+), $n_{max}$ 3250, 1615, 1520, 1220, 1080, 870 cm$_{-1}$. $d_H$(d$_6$-DMSO): 8.55d(J=4.8), 7.35t(J=8.0), 7.34d(J=8.0), 7.97d (J=8.0), 6.95t(J=8.0), 6.98d(J=8.0), 7.42d (J=4.8), 6.82d (J=8.0), 2.4s(Me), 10.4s (NH). $d_c$ (d$_6$-DMSO): 150.2, 147.0, 140.4, 139.9, 136.6, 132.0, 131.1, 124.2, 121.3, 120.4, 118.2, 115.9, 115.6, 106.2, 102.7, 13.7.

II. Synthesis of pyrido[2,3,4-kl]acridine 10 (R=H)

As illustrated in Scheme III, FIG. 2 (C), the same synthesis as Compound 9 was followed. Starting material 2, as described by Heidelberger, *J. Am. Chem. Soc.*, 39, 1448 (1917), was reacted in the Skraup reaction, with vinylphenylketone to give a mixture of 4 and an undesired isomer in ratio of 1:4. Compound 4 was separated from its isomer by flash silica gel chromatography (CHCl$_3$—MeOH).

Compound 4 Amorphous powder, C$_{17}$H$_{14}$N$_2$O (m/z 262), n$_{max}$ 1645, 1600, 1485, 1000, 980 cm$^{-1}$. d$_H$(CDCl$_3$): 8.85d, (J=4.2 Hz), 7.96d(8.0), 7.70d(8.0), 7.4m(6H), 7.19d(4.2), 1.42s(Me). d$_c$(CDCl$_3$): 169.5, 148.1, 146.5, 138.9, 137.3, 129.1, 128.9, 128.2, 126.4, 125.7, 124.0, 123.6, 123.1, 114.8, 24.1(Me).

Compound 6 An oil, C$_{15}$H$_{12}$N$_2$ (m/z 220), d$_H$(CDCl$_3$): 8.78d(4.3), 7.59t (8.2), 7.40m(6H), 7.02d(4.3), 6.63d(8.2). d$_c$(CDCl$_3$): 153.4, 140.8, 143.1, 141.6, 134.6, 134.1, 131.6, 126.8, 126.2, 124.7, 120.7, 118.1, 115.1.

Compound 8 Dark red oil, C$_{15}$H$_{10}$N$_4$(m/z 218, M-N$_2$), n$_{max}$ 2112, 1620, 1600, 1470, 1220, 1050 cm$^{-1}$. d$_H$(CDCl$_3$): 8.89d(4.2), 7.99d(8.2), 7,71t(8.2), 7.40m(6H), 7.21d(4.2). d$_c$(CDCl$_3$): 156.8, 146.6, 145.0, 140.9, 138.9, 137.0, 135.8, 126.2, 125.3, 125.0, 121.9, 120.1, 114.7.

Compound 10 Amorphous powder, mp>300° C. (d), C$_{15}$H$_{10}$N$_2$ (m/z 218) d$_H$(d$_6$-DMSO): 8.46d(4.8), 7.49t(8.0), 7.58t(8.0), 8.08d(8.0), 7.06t(7.6), 7.17d(8.0), 7.13d(8.0), 7.48d(4.8), 6.82d(7.8), 10.5brs. d$_c$ (d$_6$-DMSO): 149.0, 146.0, 142.05, 140.0, 138.5, 133.0, 132.0, 125.0, 121.8, 118.5, 116.5, 116.0, 112.6, 106.0, 104.4.

III. ALTERNATIVE SYNTHESIS OF PYRIDO[2,3,4,-kl]ACRIDINES

Figure 2D:
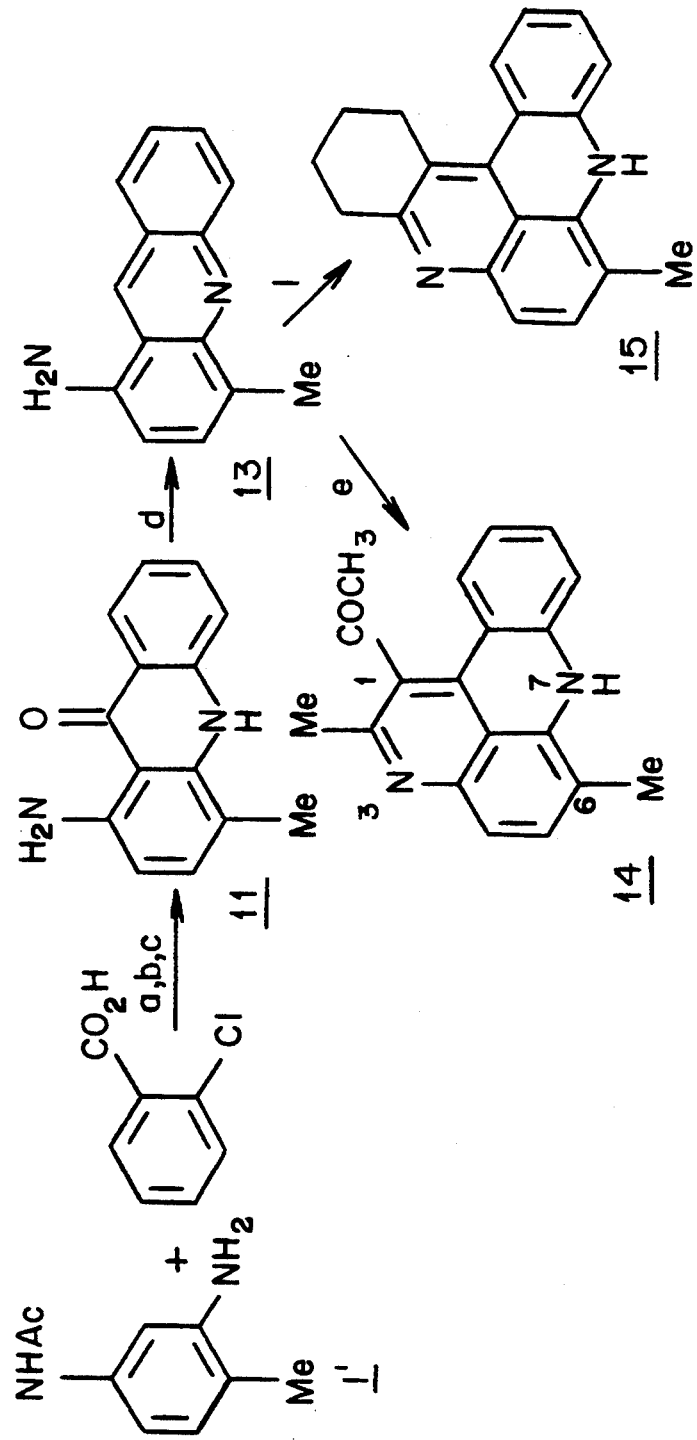
FIG. 2(D) shows Scheme IV, the steps for synthesizing compound 14, 1-acetyl-2,6,-dimethylpyrido[1,3,4-kl]acridine, and compound 15, 6-methylpyrido[2,3,4-kl]acridine.

An alternative synthesis of the pyridoacridines illustrated in Scheme IV, FIG. 2(D) started from compound 11. Compound 11 was prepared in two steps from compound 1 and o-chlorobenzoic acid, that is via an Ullmann reaction to afford a substituted diphenylamine, followed by acid catalyzed cyclization of the pyridine ring of 11 (polyphosphoric acid, 125° C., 1h).

Compound 11 was reduced with Na(Hg) to 1-amino-4-methylacridine 13 Heating compound 13 with acetylacetone and catalytic amounts of acid gave pure adduct 14, upon chromatography. Specifically, compound 14 was obtained by warming of compound 13 with acetylacetone in amylalcohol with traces of H$_2$SO$_4$ at 130° C. for 1.5 hr. The structure of compound 14 C$_{19}$H$_{16}$N$_2$O (eims, m/z 288, 100%) 1-acetyl-2,6-dimethylpyrido[2,3,4-k,l]acridine was elucidated mainly from its NMR data, by comparison of the chemical shifts with those of other pyridoacridines as described by He Hay-Yin et al., *J.O.C.*, 56, 5369 (1991). Reacting compound 13 with cyclohexanone, instead of acetylacetone, gave compound 15. Specifically, compound 15 was obtained from cyclohexanone and compound 13 under the same conditions as compound 14.

Compound 14 orange oil, C$_{19}$H$_{16}$N$_2$0 (m/z 288), n$_{max}$ 1680$^{cm-1}$, d$_H$(CDCl$_3$) 7.59brs(NH), 7.52d(J=8 Hz), 7.36d(J=8.0), 7.30t(J=8.0), 7.28d(j=8.0), 7.01d(J=8.0), 6.89t (J=8.0), 2.53s, 2.48s,2.26s. d$_c$ 208.7s,154.3s, 147.3s, 140.5s, 135.8s, 134.2s, 133.2d, 131.6d, 127.7d, 124.1s, 121.2d, 116.3s, 116.2d, 116.0s, 115.8d, 110.8s, 95.7s, 32.4q, 23.6q, 16.4q.

Compound 15, orange oil; C$_{20}$H$_{18}$N$_2$ (m/z), d$_H$(CDCl$_3$): 8.05d(J=8.2), 7.29m, 6.94m, 3.11t (J=6.0), 3.04t(J=6.0), 2.36s, 1.89m, 1.66m.

Figure 2E:
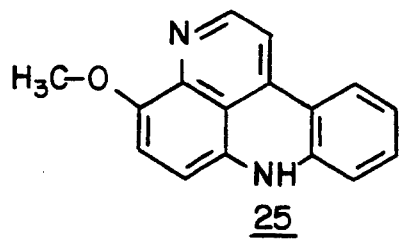
FIG. 2(E) shows the structure of compound 25, 12-demethyl-carboxylate Norsegoline.

In a similar way the inventors also synthesized 12-demethyl-carboxylate Norsegoline, compound 25 as illustrated in FIG. 2(E); n.m.r.:3.98s(OCH$_3$), 8.70d(J=4.6), 6.8–8.0m, 8.5br(NH).

Figure 2F:
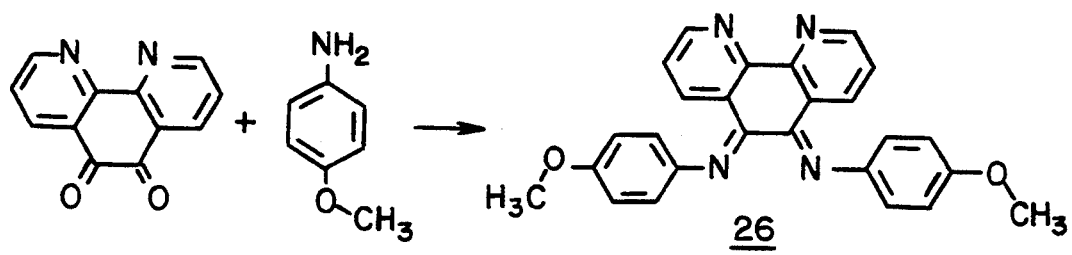
FIG. 2(F) shows the synthesis of compound 26, a seco Eilatin from 1,8-phenathroline-5,6-dione.

In other syntheses illustrated in FIG. 2(f) the inventors used 1,8-phenanthroline-5,6-dione, as described by Gillard et al., *J. Chem. Soc.*, (A), 1447–1459 (1970) to synthesize a series of seco Eilatins 26: m/e 420 (100%); δ=9.61 dd, 9.25 dd, 9.14dd, 8.32d, 8–7.0m, 3.76s, 3.59s.

Figure 2G:
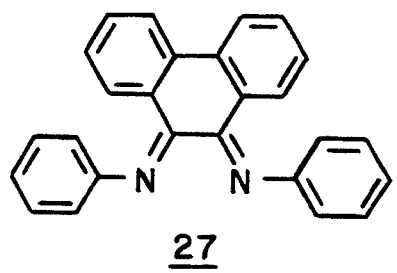
FIG. 2(G) shows the structure of compound 27, a seco Eilatin synthesized from 9,10-phenantrenequinone.

In the same way starting from 9,10-phenantrenequinone the inventors synthesized 27 as shown in FIG. 2(G); m/e 418(100%); δ=9.30dd, 8.79d, 8.63dd, 8.31d, 8.03d, 7.91–7.30m, 3.66s, 3.61s.

Figure 2H:
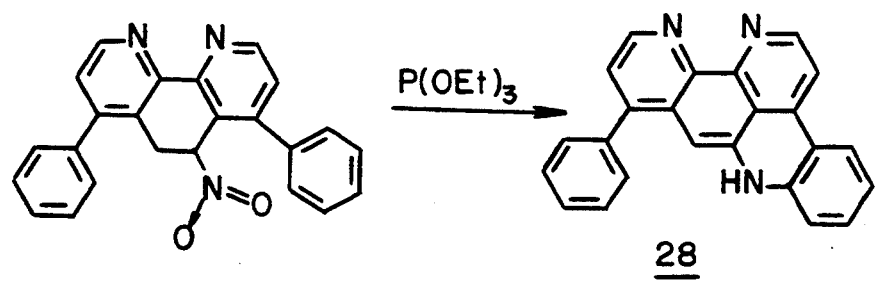
FIG. 2(H) shows the synthesis of compound 28, monodiazaeilatin (or phenylascididenine) from 5-nitro-4,5-diphenyl-phentroline via a nitrene intermediate.

Another synthesis illustrated in FIG. 2(H) was performed leading to synthetic monodeazaeilatin, compound 28 (or phenylascididemine, as described by Kobayashi et al., *Tetrahedron Lett.*, 29, 1177–1180 (1988)) from 5-nitro-4,5-diphenyl-phenantroline, via a nitrene intermediate, as described by Wentrup, "Reactive Molecules", 4, 162–264, John Wiley, New York (1984); and Cadogen, *Quart. Rev. Chem. Soc. London*, 2.2, 222–251 (1968). Compound 28, δ=8.80d(J=5.0), 8.70d(5.0),7.73d(8.0),7.43m, 7.20m, 6.90m, 6.63s (1H).

IV. Nitration and hydrogenation of Eudistoma Alkaloids

Figure 2I:
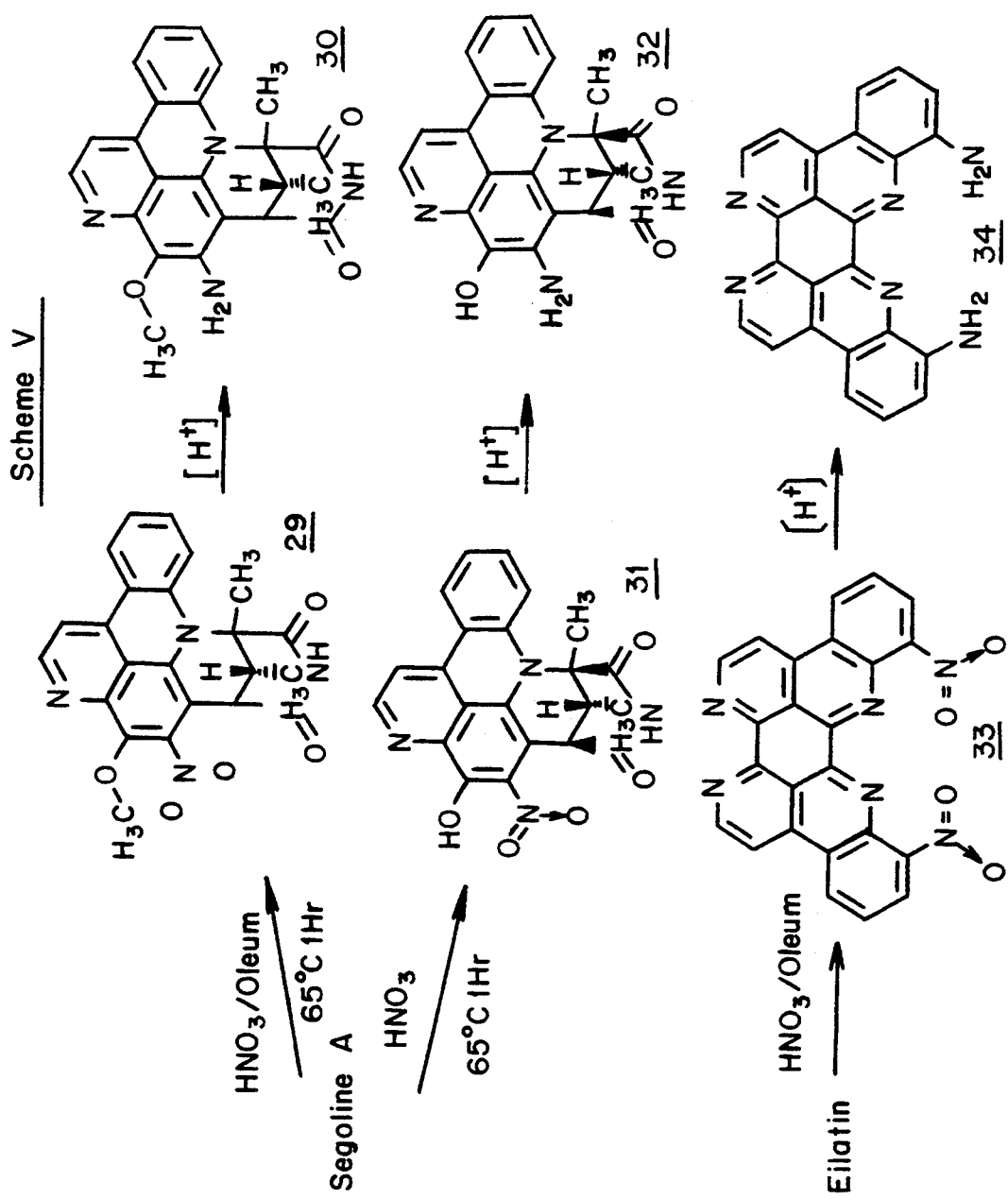
FIG. 2(I) shows Scheme V, the selective nitration of Segoline A & B and of Eilatin followed by reduction of the resulting nitro groups to yield the corresponding amino compound.
Figure 3A:
FIG. 3 is a series of phase-contrast micrographs showing the long-term effects of the Eudistoma alkaloids on morphological appearance of living mouse neuroblastoma N1E-115 cells. A,B: Untreated cells, 3 (A) and 8 (B) days after subculture. C,D: Cells grown for 3 (C) and 8 (D) days with 12.8 μM Debromoshermilamine. E,F: Cells grown for 7 days with Isosegoline A (39 μM) and Norsegoline (16.3 μM), respectively.
Figure 3C:
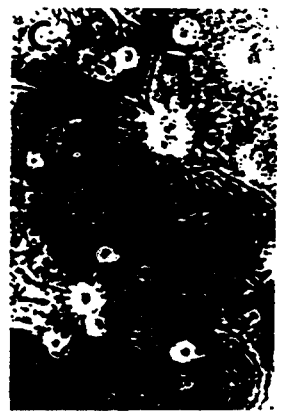
Figure 3E:
Figure 3B:
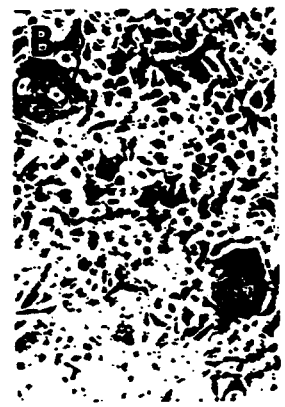
Figure 3D:
Figure 3F:
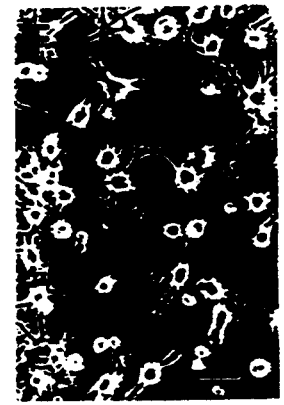
Figure 5D:
FIG. 5 is a series of Hoffman Modulation Contrast micrographs showing the long-term effects of the two synthetic pyridoacridines, 4-methylpyrido[2,3,4-kl]acridine and pyrido[2,3,4-kl]acridine on morphological appearance of N1E-115 cells. Cells were grown for six days in the absence of drugs (A), or in the presence of: 10 μM 4-methylpyrido[2,3,4-kl]acridine (B), 4 μM pyrido[2,3,4-kl]acridine (C), 0.08 μM Eilatin (D), 75 μM forskolin (E).
Figure 5E:
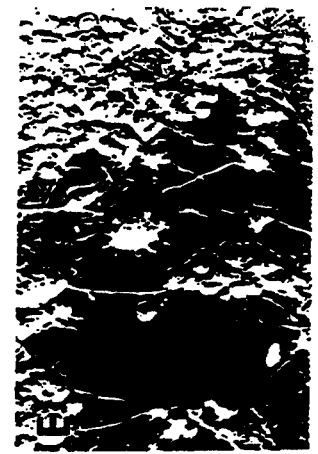
Figure 5B:
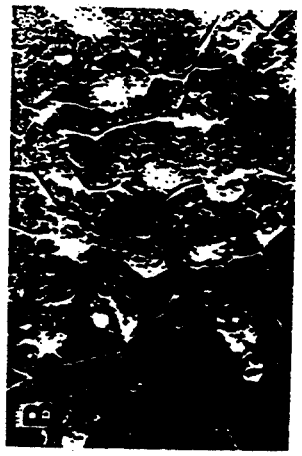
Figure 5C:
Figure 5A:
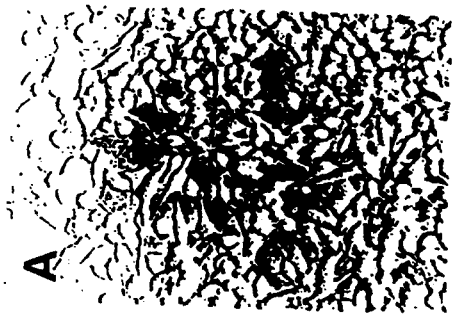
Figure 6A:
FIG. 6 is a series of phase-contrast micrographs showing the effects of the Eudistoma alkaloids on morphological appearance of NIL8 fibroblast cells. Cells were grown for 5 days in the absence of drugs (A), and in the presence of 25 μM forskolin (B), 1.4 μM Eilatin (C), or 12.8 μM Debromoshermilamine (D).
Figure 6C:
Figure 6B:
Figure 6D:

As illustrated in Scheme V, FIG. 2(I) nitration of Segolina A & B yielding compound 29, 31 and of Eilatin yielding compound 33 is carried out, followed by reduction of the resulting nitro groups to yield the corresponding amino compounds 30, 32 and 34. For example, Eilatin has been demonstrated to afford selectively the 4,7-dinitro derivative 33. Reduction of the nitro group yields the corresponding amino groups 34 from which a variety of derivatives are prepared (—OH, halogens, —CN, —CO$_2$H, etc.) via the diazonium ion. The regioselectivity of nitration (to C-14 in case of Segoline A and Segoline B, and C-4 and C-7 in case of Eilatin) has already been demonstrated. Hydrogenation, with H$_2$, dithionite or Sn or Fe/HCl reduction of the nitro compounds affords the amino derivatives. The amines are further modified via diazonium salts (NaNO$_2$—HCl), and then changed into different groups using well established procedures for these compounds, (e.g. halogens, —CN) other nitration reagents, such as NO$_2$BF$_4$, HNO$_3$-acetic acid, HNO$_3$—H$_2$SO$_4$ at suitable reaction conditions are also used to achieve other substitutents. Many of the resulting new compounds are amenable to further chemical changes.

Example V

Cell Biological Studies

A. Effects of the Eudistoma alkaloids and synthetic pyridoacridines on neuroblastoma cells.

Experiments to evaluate the biological activities of the six (6) novel Eudistoma alkaloids and the two (2) synthetic pyridoacridines, 4-methylpyrido[2,3,4-kl]acridine and pyrido[2,3,4-kl]acridine, were first carried out on cells of the mouse C1300 neuroblastoma clone N1E-115 supplied by Dr. Nirenberg, see Amano T., Richelson, E., and Nirenberg M. *Proc. Natl. Acad. Sci. USA*, 63, 258–263 (1972). The inventors chose the neuroblastoma N1E-115 cells because these tumor-derived cells can be induced to express characteristic neuronal properties by a variety of procedures see Spector, "Electrophysiology of clonal nerve cell lines. In: Excitable Cells in Tissue Culture", Nelson et al. eds., *Plenum*, New York 247–277 (1981) and can serve as a useful experimental system in which to explore the effects of the Eudistoma alkaloids on the biological properties of both cancer cells and neuronal cells.

The N1E-115 cells were exposed to various concentrations of the six (6) natural products shown in FIG. 1, and of the two synthetic pyridoacridines shown in Scheme III of FIG. 2. All the compounds completely inhibited cell proliferation and induced neuronal differentiation. FIG. 3 is a series of phase-contrast micrographs showing the long-term effects of the Eudistoma alkaloids on morphological appearance of living mouse neuroblastoma N1E-115 cells. A,B: Untreated cells, 3 (A) and 8 (B) days after subculture. C,D: Cells grown for 3 (C) and (8) days with 12.8 $\mu$M Debromoshermilamine. E,F: Cells grown for 7 days with Isosegoline A (39 $\mu$M) and Norsegoline (16.3 $\mu$M), respectively. FIG. 5 illustrates the appearance of N1E-115 cells 6 days after replating in the absence (A) and in the presence of 10 $\mu$M 4-methylpyrido[2,3,4-kl]acridine (B), or 4 $\mu$M pyrido[2,3,4-kl]acridine. While the untreated cells continued to divide and reached confluence, the treated cells stopped dividing, and their appearance changed dramatically. They flattened onto the surface, increased considerably in size, and extended long neurites to resemble mature neurons. These effects were not readily reversible and following removal of the drugs cell division did not recommence for more than a week and the cells maintained their differentiated morphology. For each of the eight (8) compounds a range of concentrations was determined that inhibited cell proliferation and induced morphological differentiation (defined as enlargement of cells and outgrowth of neurites).

The range of effective concentrations for Segoline A, Segoline B and Isosegoline A was 12–52 $\mu$M, for Norsegoline and Debromoshermilamine it was 8–40 $\mu$M and 6–32 $\mu$M, respectively, and for Eilatin which was the most potent of the compounds, it was 0.05–0.5 $\mu$M. The range of effective concentrations for the two synthetic pyridoacridines, 4-methylpyrido[2,3,4-kl]acridine and pyrido[2,3,4-kl]acridine was 7.5–12.5 $\mu$M and 2–5 $\mu$M, respectively. In each case exposure of N1E-115 cells to concentrations below this range was without a noticeable effect, and above this range the compounds were cytotoxic. Within the effective range the degree of inhibition of cell division was dependent on the concentration used. At higher concentrations cell division was completely halted and some cell death was observed. At lower concentrations cell division continued, but at a much slower rate.

Although all eight (8) alkaloids inhibited cell proliferation and caused profound alterations in cell morphology, there were interesting differences between the alkaloids in regard to their effects on cell appearance. Thus, Debromoshermilamine treatment gave rise to a large proportion of very flat cells of considerable size and relatively few neurites, norsegoline induced relatively small cell bodies and numerous long neurites, Segoline A and B, Isosegoline A, Eilatin and pyrido[2,3,4-kl]acridine induced flattened cell bodies as well as numerous long neurites, and with 4-methylpyrido[2,3,4-kl]acridine most neurites were short. These qualitative differences raise the possibility that the eight (8) alkaloids do not exert their effects on cell growth and differentiation via a common mode of action.

B. Comparison with agents that mimic or elevate cAMP.

Since most treatments that inhibit cell proliferation and induce morphological differentiation in neuroblastoma cells involve a rise in intracellular cAMP levels, as reviewed by Schubert, "Developmental Biology of cultured Nerve, Muscle and Glia", Ch 3 pp 72–165, John Wiley & Sons, New York (1984), the effects of the Eudistoma alkaloids were compared to those of extensively used agents that mimic cAMP or elevate its levels. This comparison showed short-term similarities, but revealed striking long-term differences between the Eudistoma alkaloids and the cAMP-related agents. These differences are illustrated in FIG. 4 which compares the effects of the adenylyl cyclase activator forskolin to those of Segoline A, and Eilatin. FIG. 4 is a series of phase-contrast micrographs showing the long-term effects of forskolin and the Eudistoma alkaloids on morphological appearance of N1E-115 cells. A,B: Untreated cells 3 (A) and 6 (B) days after subculture. C,D: Cells grown for 3 (C) and 6 (D) days with 50 $\mu$M forskolin. E,F: Cells grown for 3 (E) and 6 (F) days with 39 $\mu$M Segoline A. G,H: Cells grown for 3 (G) and 6 (H) days with 0.14 $\mu$M Eilatin. As shown in the upper panel of FIG. 4, cells that have been exposed for 3 days to either 50 $\mu$M forskolin (C), 39 $\mu$M Segoline A (E) or 0.14 $\mu$M Eilatin (G), appeared remarkably similar. All three treatments inhibited cell division and induced morphological differentiation. However, with time in culture, the effects of a single forskolin application waned, the cells resumed cell division and, as shown in FIG. 4 at (D) after 6 days incubation, became confluent like the control cells (B). In contrast, a single application of Segoline A or Eilatin induced a dramatic transition to a more homogeneous state in which cell division is completely blocked and, as shown in FIG. 4 at (F,H), after 6 days the cells assumed the characteristic appearance of mature neurons.

The transient effects of forskolin on cell growth and differentiation were also obtained with a single application of 1 mM dbcAMP plus 1 mM theophylline, and with the potent site-selective cAMP analogues 8-chloro cAMP (250 $\mu$M) and CPT-cAMP (250–500 $\mu$M). The inventors' finding that the fully morphologically differentiated state can be reached and maintained by a single application of the Eudistoma alkaloids suggests that these compounds act on the cAMP signaling system in a different manner than that of cAMP whose levels must remain continuously high to sustain inhibition of cell division and neurite outgrowth.

C. Effects of the Eudistoma Alkaloids on growth and morphology of normal and virus-transformed fibroblasts.

To obtain further evidence for the involvement of the cAMP signaling system in the growth regulatory properties of the Eudistoma alkaloids, the effects of the eight (8) alkaloids were tested on growth and morphology of the normal hamster fibroblast NIL8 cell line and of NILS-HSV cells, a derivative of NIL8 cells that has been transformed by hamster sarcoma virus see Hynes et al., Cell, 13, 151–163 (1978). As reviewed by Willingham, Int. Rev. Cytology, 44, 319–363 (1976) normal fibroblasts respond to cAMP elevation by showing slower growth rates, lowered saturation densities and by becoming flatter and more elongated than usual. Transformed fibroblasts which display altered growth patterns and aberrant morphologies respond to cAMP elevation by restoration of many normal aspects of growth and morphology, a phenomenon known as "cAMP-mediated reverse transformation" as described by Lockwood et al., J. Cell. Biochem., 33, 237–255 (1987).

FIG. 6 is a series of phase-contrast and FIG. 7 is a series of Hoffman Modulation Contrast micrographs showing the long-term effects of the Eudistoma alkaloids and forskolin on morphological appearance of NIL8 cells. In FIG. 6 NIL8 cells were grown for 5 days in the absence of drugs (A), or in the presence of 25 μM forskolin (B), 1.4 μM Eilatin (C) or 12.8 μM Debromoshermilamine (D). As illustrated, a single application of 1.4 μM Eilatin or 12.8 μM Debromoshermilamine to NIL8 cells produced effects which are strikingly similar to those obtained by chronically treating time cells with agents that elevate or mimic cAMP. The cells increased considerably in size, became more elongated (C) or flatter (D) than usual, their growth was inhibited and because of their large size they reached very low saturation densities. It should also be noted that the concentration of Eilatin used (1.4 μM) was toxic to both the transformed cell lines indicating that the normal cells are less sensitive to this alkaloid. FIG. 6B shows that the effects of a single forskolin application were transient such that after 5 days the cells reached the high saturation densities typical of untreated cultures (A). As shown in FIG. 7 NIL8 cells were grown for six days in the absence of drugs (A), or in the presence of 10 μM 4-methylpyrido[2,3,4-kl]acridine (B), 4 μM pyrido[2,3,4-kl]acridine (C), 0.08 μM Eilatin (D), or 75 μM forskolin (E). As illustrated in this figure a single application of the two synthetic pyridoacridines 4methylpyrido [2,3,4-kl ]acridine and pyrido [2,3,4-kl]acridine produced effects which were similar to those produced by the natural alkaloids, whereas a single application of 0.08 μM Eilatin, a concentration that produced differentiation in N1E-115 cells and (FIG. 5 at D), and reverse transformation in NIL8-HSV cells (see below FIG. 10 at D) had no effects on NIL8 cells. This predilection towards cancer cells is a very desirable property in developing potential drugs for the treatment of cancer.

FIG. 8 is a series of Hoffman Modulation Contrast micrographs showing the effects of time Eudistoma alkaloids on morphological appearance of the HSV-trans formed NIL8 fibroblasts (NIL8-HSV). A–D show cells grown for 6 days in the absence of drugs (A), or in the presence of 75 μM forskolin (B), 13 μM Segoline B (C) or 0.21 μM Eilatin (D). E and F show the appearance of the Segoline B- and Eilatin-treated cells, 7 days after removal of the toxins.

Figure 9A:
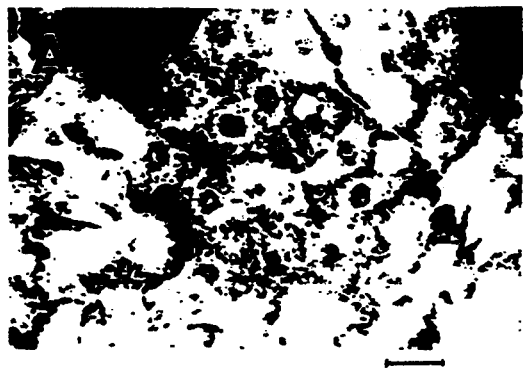
FIG. 9 shows fluorescence micrographs of fixed $NIL_8$-HSV cells stained with rhodamine-phalloidin to illustrate the effects of Segoline B on F-actin organization. A: F-actin staining in control cells. B: F-actin staining in a cell treated for 4 days with 13 μM Segoline B.
Figure 9B:
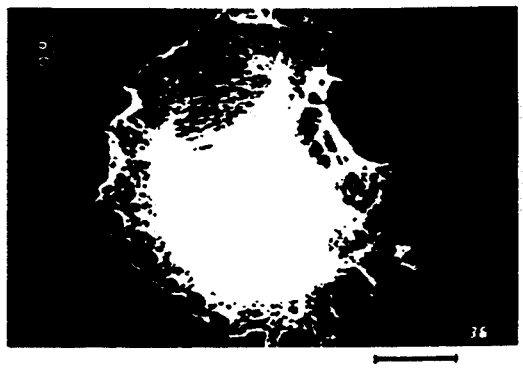
Figure 7D:
FIG. 7 is a series of Hoffman Modulation Contrast micrographs showing the effects of the two synthetic pyridoacridines, 4-methylpyrido[2,3,4-kl]acridine and pyrido[2,3,4-kl]acridine on morphological appearance of NIL8 fibroblast cells. Cells were grown for 6 days in the absence of drugs (A), or in the presence of 10 μM 4methylpyrido[2,3,4-kl]acridine (B), 4 μM pyrido[2,3,4-kl]acridine (C), 0.08 μM Eilatin (D), or 75 μM forskolin (E).
Figure 7E:
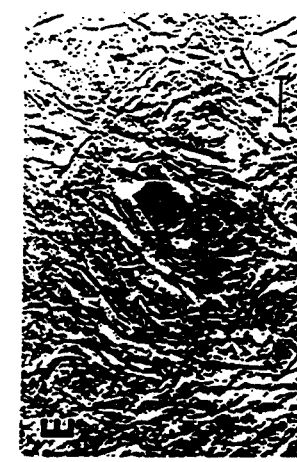
Figure 7B:
Figure 7C:
Figure 8A:
FIG. 8 is a series of Hoffman Modulation Contrast micrographs showing the effects of the Eudistoma alkaloids on morphological appearance of the HSV-transformed NIL8 fibroblasts (NIL8-HSV). A-D Cells grown for 6 days in the absence of drugs (A), or in the presence of 75 μM forskolin (B), 13 μM Segoline B (C) or 0.21 μM Eilatin (D). E and F show the appearance of the Segoline B- and Eilatin-treated cells, 7 days after removal of the toxins.
Figure 8C:
Figure 8E:
Figure 8B:
Figure 8D:
Figure 8F:
Figure 10D:
FIG. 10 (A-E) is a series of Hoffman Modulation Contrast micrographs showing the effects of the two synthetic pyridoacridines, 4-methylpyrido[2,3,4-kl]acridine and pyrido[2,3,4 -kl]acridine on morphological appearance of the virus-transformed NIL8-HSV fibroblast cells. Cells were grown for 6 days in the absence of drugs (A), or in the presence of 10 μM 4-methylpyrido[2,3,4-kl]acridine (B), 4 μM pyrido[2,3,4-kl]acridine (C), 0.08 μM eilatin (D), or 75 μM forskolin (E).
Figure 10E:
Figure 10B:
Figure 10C:
Figure 10A:

As illustrated in FIG. 8 at A, this tumor cell line displays alterations in cell growth and morphology that is characteristic of many oncogenic, transformed cell lines. The morphology of a 6 day old culture is disorganized, the cells are small, have rounded or spindle-like shapes indicated a decreased adhesion to the substratum, and can pile up due to a loss of contact inhibition. Another characteristic feature of the transformed phenotype, the disruption of cytoskeletal organization that governs cell morphology, is illustrated in FIG. 9 (at A–B). FIG. 9 (at A and B) shows a pair of fluorescence micrographs of fixed NIL8-HSV cells stained with rhodamine-phalloidin to show the effects of Segoline B on F-actin organization. A: F-actin staining in control cells. B: F-actin staining in a cell treated for 4 days with 13 μM Segoline B. As seen in this figure, the fluorescent-staining patterns of F-actin (labeled with rhodamine-phalloidin) in 4 days old untreated NIL8-HSV cells are diffuse and lack the normal system of microfilament bundles (stress fibers) see Spector et al., "Cell Motility and the Cytoskeleton", 13, 127–144 (1989). A single application of forskolin (50-100 μM) to NIL8-HSV cultures can transiently reverse the effects of transformation, so that the cells acquire normal growth and morphology, and assemble stress fibers (data not shown). However, as shown in FIG. 8 at B, with time in culture the cells reverted to the transformed phenotype. In contrast, one application of 13 μM Segoline B or 0.21 μM Eilatin was sufficient to permanently reverse the effects of transformation. As illustrated in FIGS. 8 at C and D, and in FIG. 9 at B the Eudistoma alkaloids had dramatic effects on cell shape and actin organization. The treated cells became large and flat and showed the typical network of stress fibers like their normal counterparts see Spector et al., "Cell Motility and the Cytoskeleton", 13 127–144 (1989) Furthermore, the cells maintained their reduced growth and flattened morphology even seven (7) days after drug removal (FIG. 8 at E, and F). As illustrated in FIG. 10 at B–D, similar effects on NIL8-HSV cells were obtained with 4-methylpyrido[2,3,4-kl]acridine, pyrido[2,3,4-kl]acridine and with a lower concentration of Eilatin (0.08 μM) which did not exert any effect on the normal NIL8 cells.

Example VI

Biochemical studies

The results of the cell biological studies show that the six (6) new alkaloids isolated from the Red Sea tunicate Eudistoma sp. and the two synthetic pyridoacridines represent a new class of powerful growth regulatory compounds that cause growth inhibition, differentiation and reverse transformation in cancer cell lines. The results further suggest that these compounds act on the cAMP signaling system. To obtain more direct evidence for this hypothesis, time inventors chose to assess the effects of the Eudistoma alkaloids on three well-characterized metabolic systems regulated by cAMP. These include:

1. Activity of pyruvate kinase—a key glycolytic enzyme whose activity is inhibited by cAMP-dependent phosphorylation.
2. Induction of mRNA for P-enolpyruvate carboxykinase (PEPCK)—a key enzyme in the gluconeogenesis pathway in liver and kidney cells whose gene transcription rate is stimulated by cAMP see Hod et al., *N.Y. Acad. Sci.*, 478, 31–45 (1986) and Hod et an., *J. Biol. Chem.*, 263, 7747–7752 (1988).
3. Growth hormone release from anterior pituitary cells which is stimulated by a number of hormonal factors that activate the adenylyl cyclase system and elevate cellular cAMP levels, see, Bilezikjian et al., *Endocrinology*, 113, 1726–1731 (1983); Ray et al., *Mol. Cell. Endocrinology*, 45, 175–182 (1986) and Gabriel et al., *Neuroendocrinology*, 50 170–176 (1989).

Figure 11:
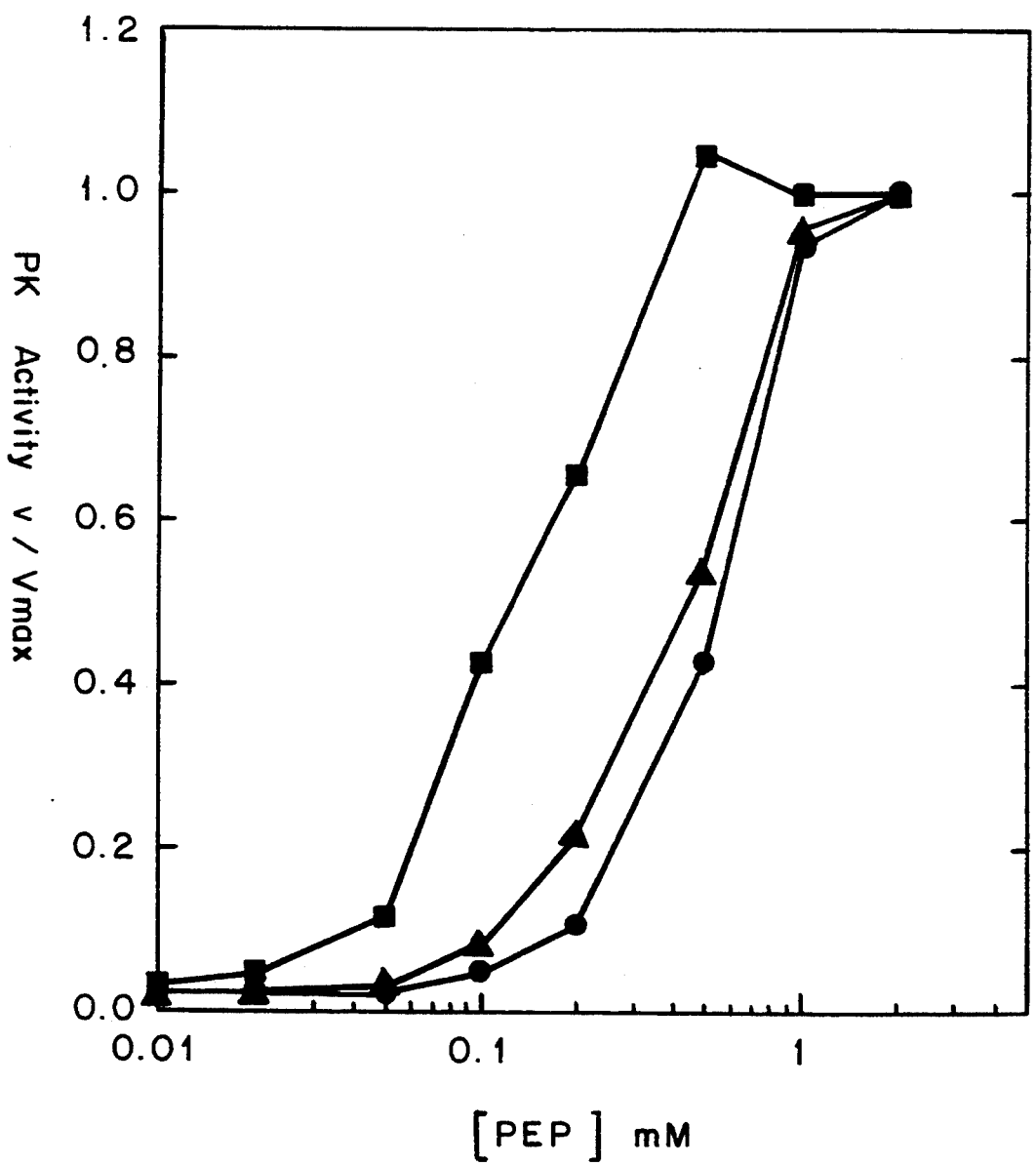
FIG. 11 is a graph showing the effects of the Eudistoma alkaloids on pyruvate kinase activity in cultured rat hepatoma FAO cells. Enzyme activity $v/V_{max}$ was assayed as described in Example IV in partially purified extracts from cells incubated for 1 h in the absence (■) or presence of 100 μM CPT-cAMP (●) and 26 μM segoline A (▲) as a function of substrate concentrations (phosphoenolpyruvate, PEP). The dashed line represents the $K_m$ for the substrate and it was 0.14 for the control, 0.52 for the cAMP analog, and 0.44 for segoline A. $K_m$'s for norsegoline and Debromoshermilamine were 0.4 and 0.46, respectively.
Figure 12:
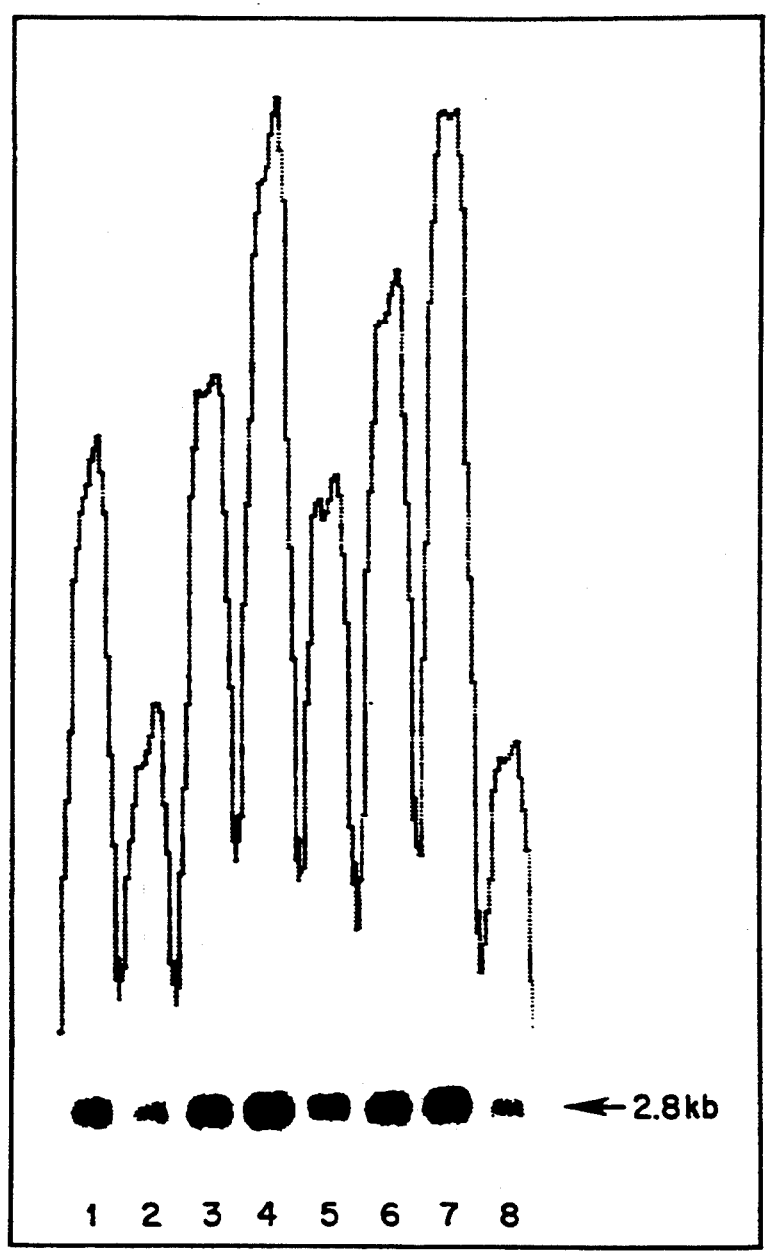
FIG. 12 is a graph showing the effects of Eudistoma alkaloids on levels of PEPCK mRNA in FTO-2B rat hepatoma cells. The cells were exposed for 4 hours to serum-free medium which contained: 5 μM CPT-cAMP (lane 1), 5, 26 and 52 μM segoline A (lanes 2–4), 2.6, 12.8 and 38.4 μM Debromoshermilamine (lanes 5–7) or to serum-free medium alone (lane 8).
Figure 13:
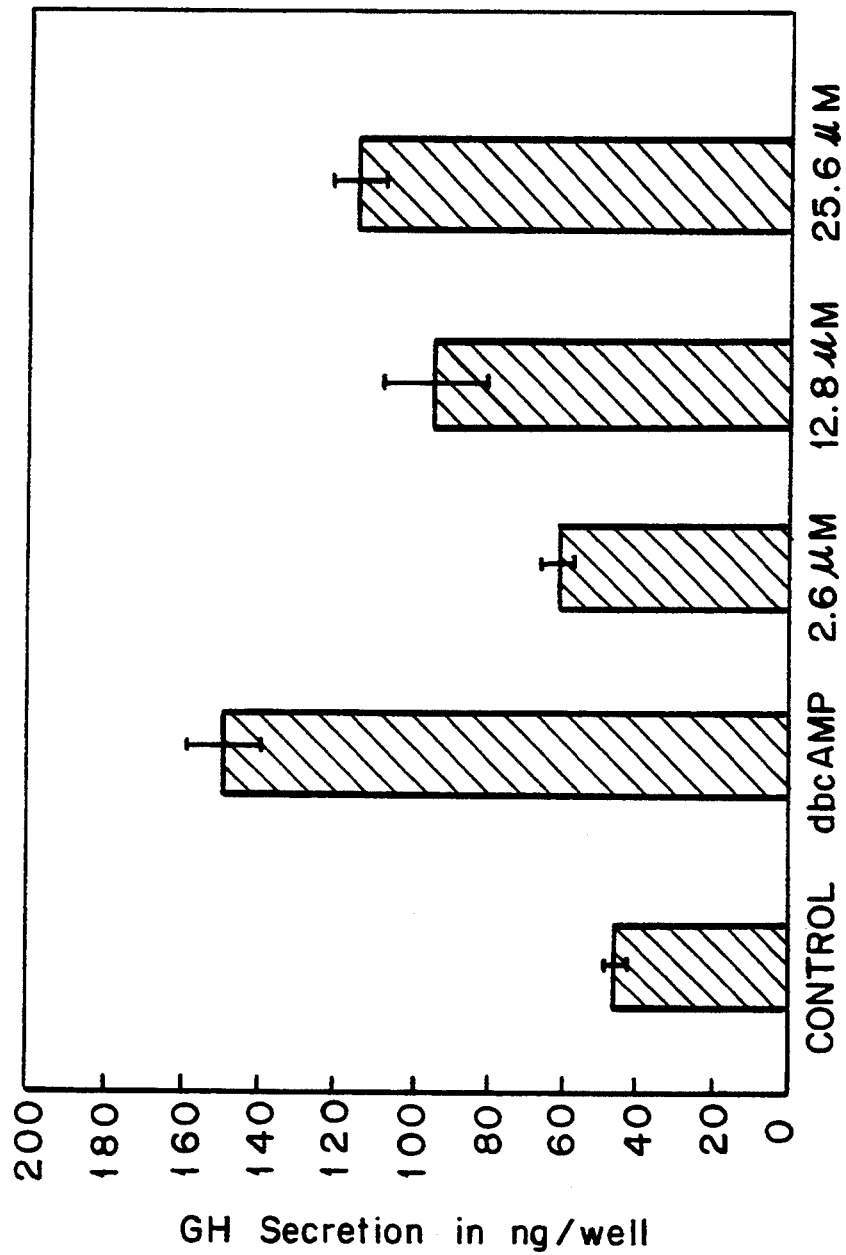
FIG. 13 is a graph showing the effects of Debromoshermilamine on the secretion of growth hormone (GH) from dispersed rat anterior pituitary cells. Each bar represents the mean ±s.e.m of four wells.

The results obtained by the inventors are summarized in FIGS. 11-13. FIG. 11 is a graph showing the effects of the Eudistoma alkaloids on pyruvate kinase activity in cultured rat hepatoma FAO cells. Enzyme activity v/Vmax was assayed in partially purified extracts from cells incubated for 1 h in the absence (squares) or presence of 100 μM 8-(4-chlorophenylthio) cyclic AMP (CPT-cAMP)-CPT-cAMP (circles) and 26 μM Segoline A (triangles) as a function of substrate concentrations (phosphoenolpyruvate, PEP). The dashed line represents the $K_m$ which measures the affinity of an enzyme to a substrate, defined as the substrate concentration that yields the half maximal reaction rate with the enzyme, for the substrate and it was 0.14 for the control, 0.52 for time cAMP analog, and 0.44 for Segoline A. $K_m$'s for Norsegoline and Debromoshermilamine were 0.4 and 0.46, respectively.

FIG. 12 is a graph showing the effects of Eudistoma alkaloids on levels of PEPCK mRNA in FTO-2B rat hepatoma cells. The cells were exposed to medium which contained: 5 μM 8-CPT-cAMP (line 4), 5, 26 and 52 μM Segoline A (lines 5-7), 2.6, 12.8 and 38.4 μM Debromoshermilamine (lines 8-10) or to control medium (line 11). The level of mRNA was determined by Northern blot analysis according to Hod et al., *J. Biol. Chem.*, 259, 15603-15608 (1984) using the plasmid pPCK10rc as a hybridization probe, and quantified by densitometric scanning of the autoradiograms which is shown on the left.

FIG. 13 is a graph showing the effects of debromoshermilamine on the secretion of growth hormone (GH) from dispersed rat anterior pituitary cells. Cells grown in 24-well multiwell plates were incubated for 3 h in fresh medium (DME) in the absence (control) or presence of 1 mM DbcAMP, and increasing concentrations of Debromoshermilamine as indicated. Hormone secretion was measured using rat GH radioimmunoassay. Each bar represents the mean ±s.e.m of four wells.

Taken together the results presented in FIGS. 11-13 show that the Eudistoma alkaloids mimic the effects of cAMP analogs in all three systems. Segoline A, Debromoshermilamine and norsegoline were found to inhibit pyruvate kinase activity at submaximal substrate concentrations, causing a ca. 3-fold rise in the $K_m$ which measures the affinity of an enzyme to a substrate, defined as the substrate concentration that yields the half maximal reaction rate with the enzyme, for substrate (phosphoenolpyruvate) (FIG. 11). Segoline A and Debromoshermilamine were found to stimulate the induction of PEPCK mRNA in a dose-dependent manner (FIG. 12). Finally, Debromoshermilamine was found to stimulate growth hormone release, again, in a dose-dependent manner (FIG. 13). Since in all cases the effects were similar to those induced by cAMP analogs, those results support the contention that the Eudistoma alkaloids constitute a new class of potent drugs that cause growth inhibition differentiation, and reverse transformation in cancer cell lines by acting on the cAMP signalling system. However, the alkaloids did not stimulate cAMP synthesis and did not directly interfere with the activity of the free catalytic subunit of the cAMP-dependent protein kinase or with the activation of the type I protein kinase holoenzyme. These results together with the striking differences between the Eudistoma alkaloids and the cAMP analogs and cAMP elevating agents on long-term cellular process, namely cell growth and differentiation, strongly suggest that the Eudistoma alkaloids affect target proteins that are associated with the cAMP signaling system in a novel and unique fashion.

Biomimetic Synthesis of Pyrido[k,l]Acridines

This Example describes a biomimetic synthesis of various pyrido[k,l]acridines, a synthesis which is likely to have a natural equivalent, and is expected to be suitable for the preparation of natural and other pyrido[k,l]acridines.

Norsegoline 35 and eilatin 40 are of special interest to the inventors because of their bio-activity, namely, regulation of cellular growth and an affect on cAMP mediated processes as described in Examples V and VI.

Figure 14A:
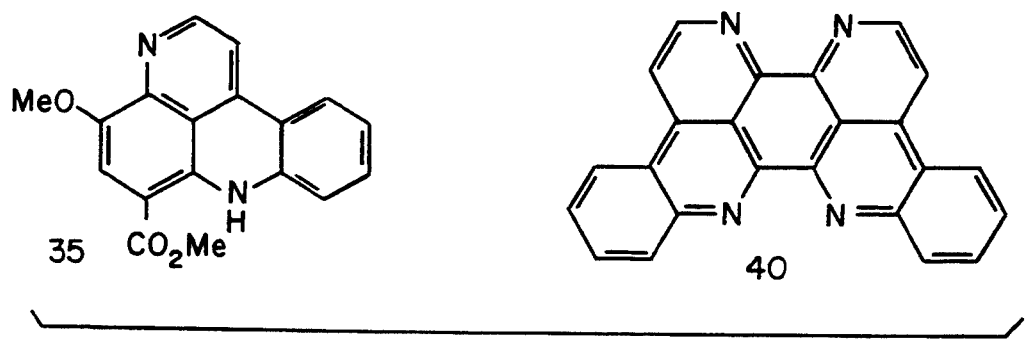
FIG. 14(A) shows the chemical structure of norsegoline and eilatin.
Figure 14B:
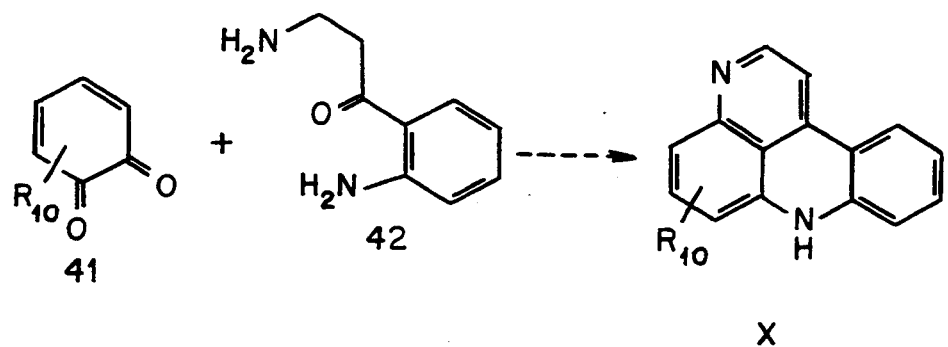
FIG. 14 (B) shows a proposed biomemetic synthesis of pyrido[k,l]acridines, particularly the compounds norsegoline and eilatin.

The inventors have determined that the most likely biomimetic synthesis of norsegoline 35 and other pyrido[k,l]acridines precursors 36, would employ the natural o-benzoquinone 41 (or the readily, in situ, oxidiseable hydroquinone) and the tryptophan matabolite kynuramine (3-amino-4orthoaminoylend-1-proyanane) as starting materials for the synthesis that is illustrated in FIG. 14(B). In FIG. 14(B) $R_{11}$ may include a substituent selected from the group of phenyl, halogen, hydroxy, $CO_2$-Methyl, HO-Methyl, $COCH_3$, $CH_3$, H, $NHOCH_3$, $NO_2$, $NH_2$ and $N_3$.

A. Synthesis of Benzo-Pyrido[k,l]Acridine 46

Figure 15:
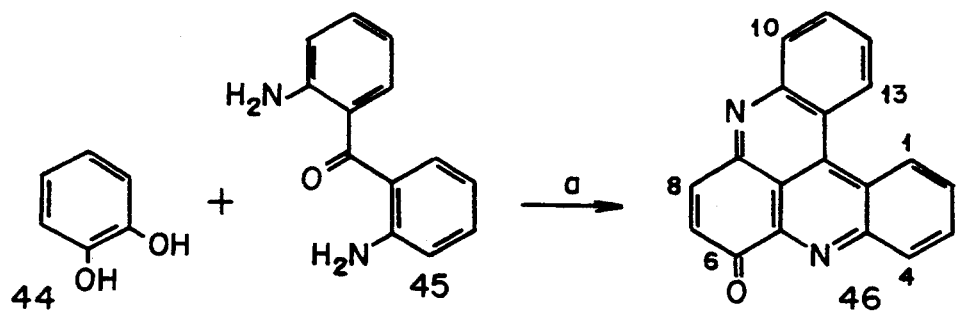
FIG. 15 shows the synthesis of benzo-pyrido[k,l]acridine.

As shown in FIG. 15, in order to avoid the competition problem between the two amino groups of 42 the inventors started this set of Examples using the symmetric 2,2′-diaminobenzophenone 45, as described by Partridge et al., *J. Chem. Soc.* (C), 632 (1962). Reacting catechol 44 with 45 under mild oxidative conditions (aq. EtOH, $NaIO_3$; e.g. as described by Tindale et al., *Aust. J. Chem.*, 37, 611 (1948) and references cited therein, and by Schafeir et al., *Chem. (Inter. Ed.)*, 10, 405 (1971), likewise other oxidants may suitably be used in the synthesis, such as $CeCl_3$ or $Fe(SO_4)_2$; this afforded adduct 46, a quinolino[k,l]acridine) possessing an iminoquinone functionality. Specifically, compound 45 and catechol 44 were combined (2:1 ratio) in aq. EtOH and stirred at room temperature for 24 hours in the presence of $NaIO_3$ (5 equivalents). The ppt was filtered and flashed through a silica gel column to afford compound 46 (15% yield). Compound 46 was analyzed and has the following physical characteristics:

Yellow crystals ($CH_2Cl_2$), mp 196°-198°, $C_{19}H_{10}N_2O$ m/z 282 (20%), νmax 1643, 1588, 1397, 1250, 980, 823 cm$^{-1}$. $\delta_H$ ($CDCl_3$, 500 MHz): 9.13d (J=8.2) & 9.11d (j=8.2) (H-1,13), 8.76d (J=8.2) & 8.38d (J=8.2) (H-4,10), 7.97m (5H), 7.05d (J=10.5, H-7). $\delta_c$ 183.9s, 149.6s, 147.9s (x2), 145.3s, 144.1d, 135.6s, 133.8d, 1.33.4d, 131.8d, 131.1d (x2), 130.3d, 129.3d, 127.5d, 127.0d, 124.4s, 121.1s, 111.1s.

Compound 46 was accompanied by 1:2 catecholamine adducts, as described in Example VIII E.

B. Synthesis of Compound 48, a Potential Precursor of Benzo-Norsegoline.

Figure 16:
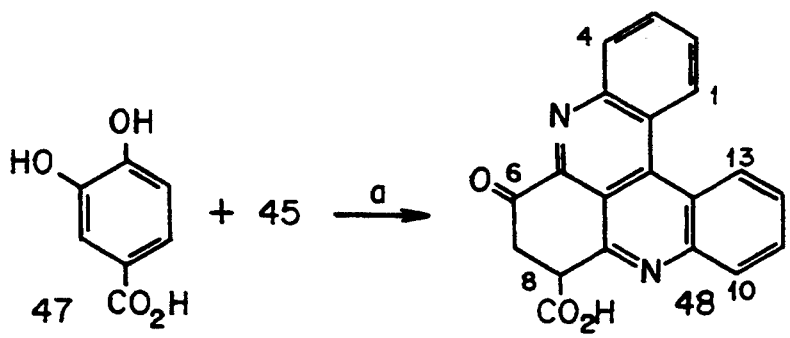
FIG. 16 shows the synthesis of compound 48, a potential precursor of benzo-norsegoline.

Compound 45 was reacted with 3,4-dihydroxybenzoic acid 47, as shown in FIG. 16, under the same conditions described in Example VII A to give in low yields (5-10%) of compound a potential precursor of benzo-norsegoline. Compound 48 was analyzed and has the following physical characteristics:

A yellow gum, $C_{20}H_{10}N_2O_3$, m/z: M-CO, 298 (47%), 298-$CO_2$, 254 (86%). νmax 3340, 1660, 1568, 1356, 1217 cm$^{-1}$, $\delta_H$($CDCl_3$-$d_4$-MeOH 9:1) 9.15d (J=8.2) & 9.02d (J=8.2) (H-1, 13), 8.69d (J=8.2) & 8.43d (J=8.2) (H-4, 10), 7.96m (4H), 7.81t (J=8.2, 1H).

Compound 48 was accompanied by 1:2 catecholamine adducts, vide infra.

C. Synthesis of 6-Oxo-Pyrido[k,l]Acridine 49

Figure 17:
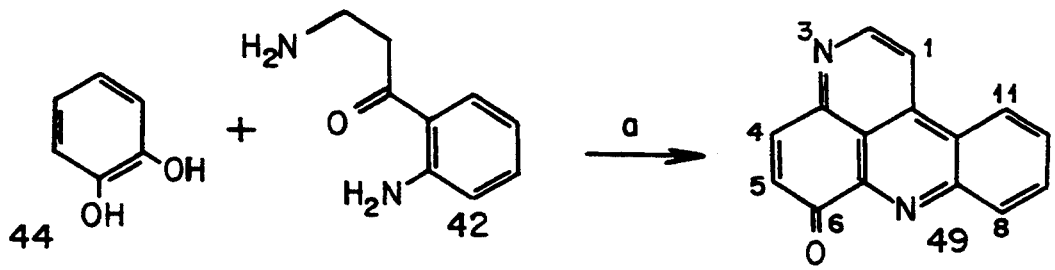
FIG. 17 shows the synthesis of 6-oxy-pyrido[k,l]acridine.

As illustrated in FIG. 17, kynuramine 42 was reacted with catechol under the same oxidative conditions described in Example VII A to afford a pyrido[k,l]acridine compound 49 (10% yield), most likely the 6-oxo (rather than 4-oxo) derivative, with accompanying 1:2, catechol-kynuramine, adducts as described in Example VII E. Compound 49 has the following physical characteristics:

A yellow gum, $C_{15}H_8N_2O$, m/z: M+2H, 234 (100%), M, 232 (22%); νmax 1647, 1621, 1578, 1340, 1272 cm$^{-1}$. $\delta_H$ (CDCl$_3$): 9.23d (J=5.6 Hz, H-2), 8.57m (2H, 11 & 1), 8.26d (J=8 Hz, H-8), 7.93t (J=8 Hz, H-9(10)), 7.86d (J=10.6 Hz, H-4(5)), 7.79t (J=8 Hz, H-10(9)), 7.04d (J=10.5 Hz, H-5(4)); $\delta_c$ (CDCl$_3$): 177.2s (CO), 151.6s, 150.2d, 147.3s, 142.3s, 142.5d, 138.0s, 134.1d, 131.8d, 131.7d, 130.2s, 129.8d, 123.0d, 121.8s, 119.5d, 117.4s.

D. Synthesis of Dihydropyrido[k,l]acridine Compound 51, and Pyrido[k,l]acridine Compound 52

Figure 18:
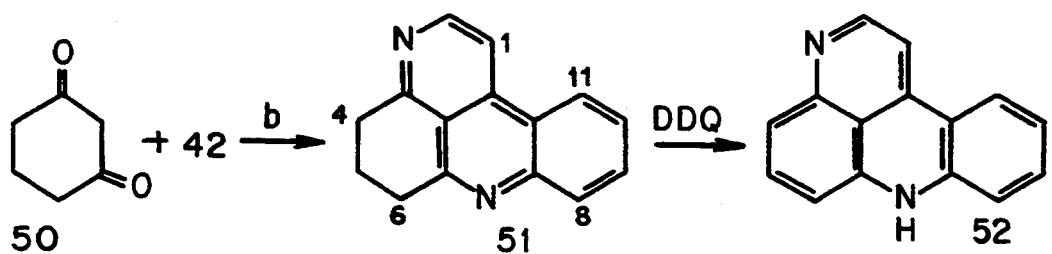
FIG. 18 shows the synthesis of dihydropyrido[k,l]acridine and pyrido[k,l]acridine.

Instead of catechol 44, 3,5-cyclohexanedione 50 (formally "dihydro-1,3-dihydroxybenzene") was reacted with kynuramine 42, as illustrated in FIG. 18, to obtain in high yield (ca. 90%) dihydropyrido[k,l]acridine 51 which by oxidation with DDQ (dichlorodicyano-p-quinone) afforded the pyrido[k,l]acridine 52, as previously described by the inventors; see Gellerman et al., Tet. Letters, 33, 5577 (1992). Specifically, kynuramine 42 was reflaxed with 1,3-cyclohexanedione 50 in the presence of an oxidant, sodium m-nitrophenylsulfonate, in acetic acid and traces of HCl for 2 hours which afforded after work up compound 51 (90% yield). Compound 51 was analyzed and found to have the following physical characteristics:

A yellow powder, $C_{15}H_{12}N_2$, m/z M, 220 (100%); $\delta_H$ (CDCl$_3$): 8.79d (J=5.7, H-2), 8.48d (J=8, H-11), 8.20d (J=5.7, H-1), 8.11d (J=8, H-8), 7.82t (J=8, H-9 or 10), 7.66t (J=8, H-10 or 9), 3.37m (4H), 2.35quin (J=6, 2H); $\delta_c$ 162.1s, 160.9s, 147.9d, 145.0s, 137.9s, 130.8d, 129.4d, 126o6d, 122.8d, 121.9s, 118.2s, 113.6d, 34.4t, 33.8t, 22.3t.

This reaction is similar to the one reported by Partridge et al. (1962), supra, between dimedone and compound 45 except for the need for an oxidant in case of compound 51, required for the aromatization, which might be the driving force of the reaction.

The scope of the reactions described in Examples VIIA–VIID are expected to be broad, namely, o-quinones, p-quinones, 2,5-dihydroxy-p-quinones, substituted derivatives of the latter compounds, as well as the corresponding hydroquinones may be used for the preparation of natural pyrido[k,l]acridines and their analogues.

E. Synthesis of 1:2 Adducts, Compounds 54 and 55, as Potential Precursors of Eilatin 40 and its Derivatives.

As mentioned in Examples VIIA and E, in some of the reactions the inventors could also identify 1:2 catechol-amine adducts. Thus, as illustrated in FIG. 19, the reaction of catechol 44 and o-aminoacetophenone 53 under the reaction conditions described in Example VIIA resulted in a 60% yield of a 1:2 adduct, compound 54. Compound 54 is asymmetric regarding the two o-amino acetophenones, namely, one molecule formed an acridine-1,2-dione system while the other stayed as an appendix of the latter heterocycle. Compound 54 was analyzed and found to have the following physical characteristics:

Orange crystals mp. 206°–208° C. (CH$_2$Cl$_2$) $C_{22}H_{16}N_2O$, m/z: 356 (25%), νmax 1686, 1668, 1612, 1529, 1261, 786 cm$^{-1}$. $\delta_H$ (CDCl$_3$): 8.38d (J=8, H-8), 8.29d (J=8, H-5), 7.98d (J=8, H-3'), 7.84t (J=8, H-7), 7.77d (J=8, H-6'), 7.71t (J=8, H-6), 7.60t (J=8, H-5'), 7.27(J=8, H-4'), 6.80s (H-3), 3.19s (Me-9), 2.73s (COMe); $\delta_c$ (CDCl$_3$) 201.1s, 182.7s, 178.6s, 152.2s, 150.9s, 146.5s, 146.4s, 137.9d, 133.6d, 132.6d, 131.7d, 130.6d, 128.6s, 127.5s, 125.3d, 124.4d, 122.0d, 119.6s, 114.9s, 102.7d, 28.2q, 15.6q.

Reacting compound 54 with BF$_3$ etherate provided, in high yields (70%), the symmetric pentacyclic dibenzo-1,10-phenantroline-5,6-dione 55. Functionalization of the two methyls of 55 is expected to lead to applicable intermediates for eilatin 40 and its derivatives. Specifically, compound 54 in CH$_2$Cl$_2$ was refluxed in the presence of BF$_3$Et$_2$O for 24 hours to afford compound 55 after work up. Compound 55 was analyzed and found to have the following physical characteristics:

An amorphous yellow powder, $C_{22}H_{14}N_2O$, m/z M+H, 339 (1%), M-2H, 336 (9%), M+H-CO, 311, (94%) M-CO, 310 (84%); νmax 1686, 1500, 1422, 1308, 1287, 896 cm$^{-1}$; $\delta_H$ (CDCl$_3$) 8.52d (J=8.2, H-1, 10), 8.30d (J=8.2, H-4,7), 7.92t (J=8.2, 2H), 7.70t (J=8.2, 2H), 3.19s (2Me's); $\delta_c$ 186.2s, 153.0s, 151.2s, 149.7s, 132.6d, 132.1d, 129.6d, 129.4s, 125.5d, 124.1s, 16.2q.

The 4,5-diamination of 1,2-quinones is in agreement with the reaction of o-benzoquinone with aniline, as described by Tindale et al. (1989) supra, and Schafeir et al. (1971) supra. However, those publications utilized biogenic amines like 2-phenylethylamine, rather than the β,β'-diaminoketones 42 and 45 used by the inventors, thus only yielding polymeric tars.

The biogenic chemistry developed in this example points to kynuramine 42 and suitable quinones or hydroquinones as potential precursors for eilatin 40, norsegoline 35 and other pyrido[k,l]acridine alkaloids.

EXAMPLE VIII

Two Step Biomimetic Total Synthesis of Eilatin

The inventors have tried many approaches in attempting to synthesize the highly bio-active molecule eilatin 40, and previously have failed.

A. Synthesis of Compounds 58, 59

Figure 20:
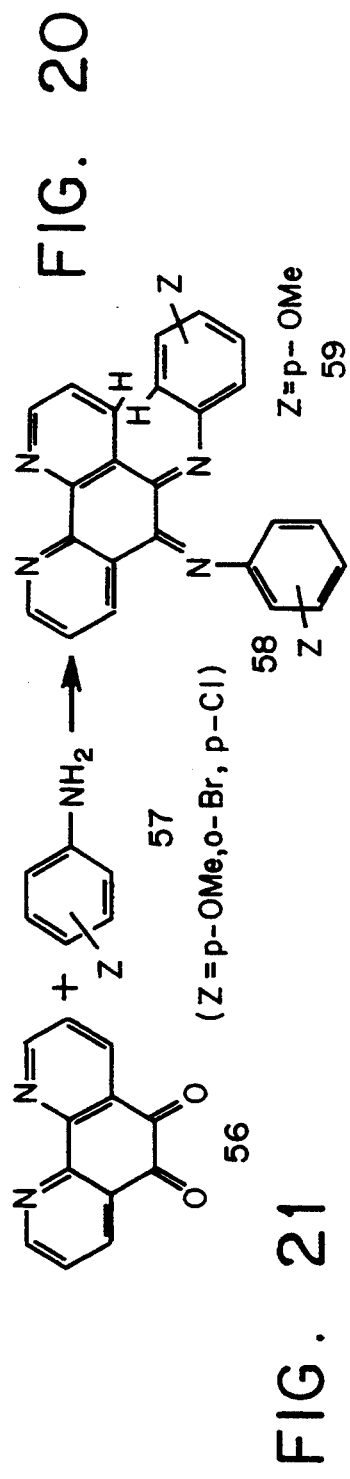
FIG. 20 shows the synthesis of compounds 58 and 59 as potential precursors of eilatin.

Thus, as illustrated in FIG. 20, the inventors have prepared from 1,10-phenanthroline-5,6-dione 56 a series of double Schiff bases 58, 59. Specifically, 1,10-phenanthroline-5,6-dione 56 was refluxed with p-anisidine 57 in acetic acid for 30 minutes. After evaporation the crude product 58 was purified on a silica gel column (65% yield); Compound 58 was analyzed and found to have the following physical characteristics:

Dark blue oil, $C_{26}H_{20}N_4O_2$, m/z M+420 (100%), 308, (75%); λmax (CH$_3$CN) 605 (13800), 430 (11100), 290 (39400); IR (KBr) 1590, 1260, 1000, 850, 810 cm$^{-1}$; $\delta_H$ (CDCl$_3$-d$_4$MeOH; 10:1): $\delta_H$ 9.61 (1H, dd, J=1.5, 3.5 Hz), 9.25 (1H, dd, J=1.5, 7.5 Hz), 9.14 (1H, dd, J=1.5, 3.5 Hz), 8.32 (1H, d, J=8 Hz), 8.01 (2H, dd, J=3.5, 7.5 Hz), 7.86 (1H, dd, J=1.5, 7.5 Hz), 7.80 (2H, d, J=9 Hz), 7.75 (1H, d, J=8 Hz), 7.46 (2H, dd, J=3.5, 7.5 Hz), 7.45 (2H, d, J=9 Hz), 7.31 (2H, d, J=9 Hz), 7.02 (2H, d, J=9 Hz), 3.76 (3H, s), 3.59 (3H, s); $\delta_c$ (5% CD$_3$OD/CDCl$_3$); 161.6s, 158.6s, 155.3s, 152.3d, 151.7d, 149.0s, 144.8s, 144.1s, 139s, 135.3d, 133.4d, 133.0d, 131.0s, 129.5s, 128.0d, 126.2s, 125.1d, 124.4d, 122.2d, 119.5s, 117.0d, 114.5d, 56.6q, 55.9q.

The inventors have tried without success to perform a double cyclisation of these molecules 58, 59 to obtain Eilatin 40.

Observation of the NMR spectra of the compound 58, specifically the spectrum of 59, a di p-methoxyphenyl deep blue compound (compare with compound 26 synthesized in Example III and illustrated in FIG. 2F) clearly pointed to a complex mixture of unsymmetrical conformers which could not easily be equilibrated by warming up 59 in solution.

B. Synthesis of Phenyl-Acididemin 64

Figure 21:
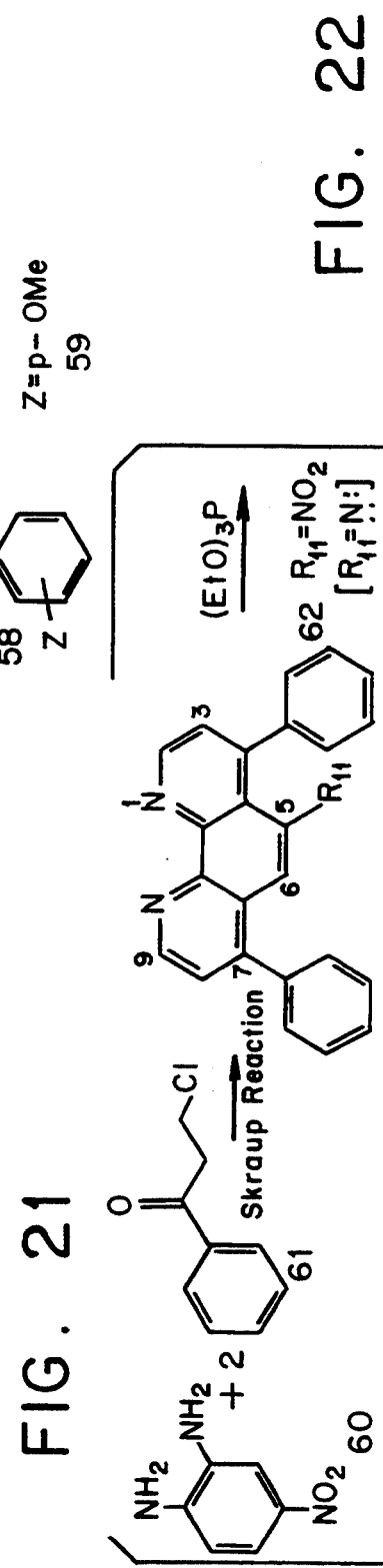
FIG. 21 shows the synthesis of phenyl-ascididemin.

In another approach illustrated in FIG. 21 the inventors performed a double Skraup reaction between 4-nitro-o-phenylenediamine 60 and two molecules of 3'-chloropropiophenone 61 to afford in ca. 15% yield 4,7-diphenyl-5-nitro-1,10-phenanthroline 62. Specifically, 4-Nitro-o-phenylenediamine 60 was reacted with β-chloropropiophenone 61 under the Skraup reaction conditions to afford in 15% compound 62, which was analyzed and found to have the following physical characteristics:

An amorphous yellow powder; m/z 377 (100%) ($C_{24}H_{15}N_3O_2$); $\delta_H$(CDCl$_3$) δ9.32 (1H, d, J=4.7 Hz), 9.26 (1H, d, J=4.7), 8.31 (1H, s), 7.70 (1H, d, J=4.7), 7.68 (1H, d, J=4.7), 7.36–7.59 (1OH, m); $\delta_c$ (CDCl$_3$): 152.2d, 150.7d, 150.18, 147.68, 147.Os, 146.78, 138.28, 136.1s, 129.5d, 129.3d, 129.Od, 128.6d, 127.88, 127.4d, 126.2d, 124.3s, 123.8d, 122.8d, 118.88; IR(KBr): 1610, 1530, 1490, 1410, 1380, 1350, 1260, 1180, 1090, 1020, 900, 850, 820, 800, 780, 760, 690, 650 cm$^{-1}$; UV (MeOH), 266, 222 nm.

Heating the solution of compound 62 in dodecane at 180° under N$_2$ for 2 hours, in the presence of (EtO)$_3$P gave via the nitrene, as reported by Cadogen, *Quart. Rev.*, 22, 122 (1968), the unexpected ketone 64 which by careful 2D NMR study (COSY, d-NOE, HMQC and HMBC) was determined to be phenyl-ascididemin. See, Kobayashi et al., *Tet. Letters*, 29, 1177 (1988), and Moody et al., *Tet.*, 48, 3589 (1992). The analysis of compound 69 disclosed the following physical characteristics:

m/z: MH$^+$360 (100%) ($C_{24}H_{13}N_3O$); $\delta_H$(d$_6$-DMSO): δ9.25 (d, H-2, J=5.0 Hz), 9.05 (d, H-5, J=5.0 Hz), 9.03 (dd, H-13, J=7.5, 1.0 Hz), 8.94 (d, H-1, J=5.0 Hz), 8.55 (d, H-6, J=5.0 Hz), 8.35 (d, H-10, J=8.0 Hz), 8.06 (dt, H-11, J=8.0, 1.0 Hz), 8.02 (dt, H-12, J=7.5, 1.0 Hz), 7.94bs (5H) (H-2'-6'); $\delta_c$ 182.1s (C8), 153.6s (C3b), 153.4s (C8a), 152.1d (C5), 150.1s (C3a), 149.8d (C2), 140.2s (C13b), 137.4d (C10), 132.3d (C11), 132Os (C7), 130.7d (C12), 128.5d (C6), 147.88 (C9a), 145.48 (C7a), 128.1–128.5 (C1'-6'), 124.5d (C13), 123.38 (C13a), 117.8d (C1), 117.7s (C3c); IR (KBr) 1682, 1600, 1428, 1201, 1170, 770 cm$^{-1}$; UV (MeOH); 366, 308, 264, 244, 219 nm.

Repeating the reaction under oxygen free argone gave the originally expected compound 63, an unstable oil, which was analyzed and found to have the following physical characteristics: $\delta_H$(CDCl$_3$): 8.89d (J=5.2), 8.73d (J=5.2) (H-2 & 5), 7.76d (J=8, H-13(10)), 7.50m (Ph), 7.27m (2H), 6.80m, (3H), 6.68s (H-8).

Under oxygen atmosphere compound 63 was transformed into compound 64. All attempts to prepare eilatin 40 from compound 63 (e.g., by reacting it under different conditions with HN3) failed.

C. Conceptional Basis for the Synthesis of Eilatin 40

From the above data and several other experiments the inventors concluded that it will be difficult if not impossible to synthesize eilatin 40, if the last step of the synthesis scheme requires cyclization of one or two aromatic rings (as in case of compounds 58 and 64, respectively) because of the severe repulsion between the protons and/or other substituents on the latter rings (both in compounds 64 and 58 the appendix phenyl(s) seem to be out of plane with the rest of the molecule). Therefore the preferred synthesis should involve closure of a piperidine ring(s) which then will readily be oxidized to the required pyridine ring(s).

Figure 22:
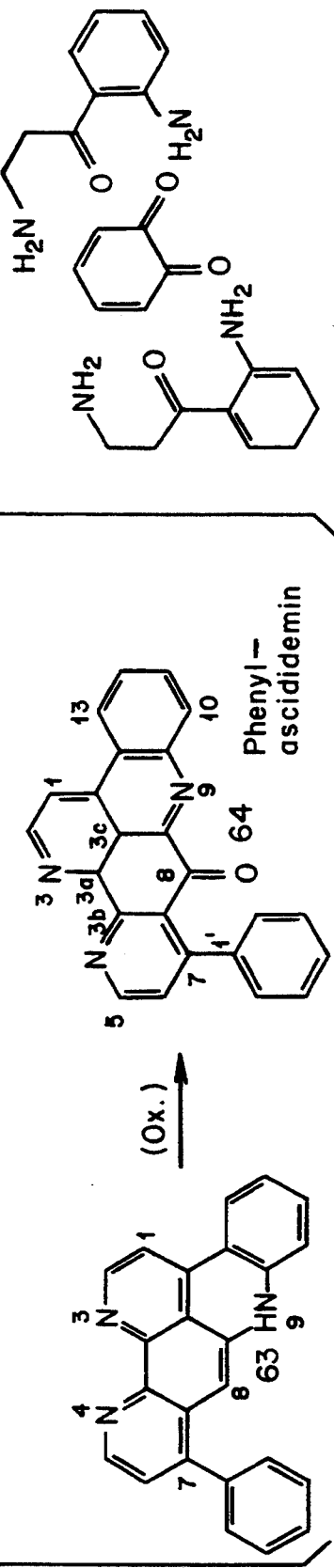
FIG. 22 shows a preferred biommetric strategy for the synthesis of eilatin.

Based on biomimetic synthesis of pyrido[k,l]acridines described in Example VII, the inventors conceived of the strategy illustrated in FIG. 22 for synthesizing eilatin 40, in which two kynamurine molecules or its derivatives are reacted with O-benzoquonine, hydroquinone or their derivatives under mild oxidative reaction conditions.

D. Two Step Biomamatic Total Synthesis of Eilatin

In carrying out the synthesis scheme for eilatin 40, described in VIII C, above, the mono protected trifluoroacetyl kynuramine 65 was reacted with catechol 44 under oxidative conditions (aq. EtOH, NaIO$_3$), as described by Tindale et al., *Aust. J. Chem.*, 37, 611 (1984) and references cited therein. This reaction afforded compound 66, whose structure was determined by 2D NMR measurements (500 MHz, COSY, HMQC, HMBC) to be a 1,2-acridinedione derivative. Specifically, in this reaction 3'-Trifluorokynuramine 65 ($\delta_H$ 7.62d (J=8, H-3), 7.24t & 6.58t (J=8, H-4,5), 6.61d (J=8, H-6), 3.76m (2H-3'), 3.19t (2H-2') was reacted with catechol 44 in aq. EtOH in the presence of 5 equivalents of NaIO$_3$,as described by Tindale et al., supra. After 24 hours the ppt was filtered and chromatographed on a silica gel column to afford compound 66 (ca. 15%), which was determined to have the following physical characteristics: mp 249°–251° C.(CH$_2$C$_2$), orange crystals, $C_{28}H_{20}F_6N_4O_5$ m/z: 606, M(1.5%), 493, M-NH$_2$COCF$_3$ (35%), 380, M-2NH$_2$COCF$_3$ (50%); vmax 3320, 1717, 1611, 1576, 1526 cm$^{-1}$; $\delta_H$ CDCl$_3$-d$_4$-MeOH 9:1): 8.52d (J=8.0, H-5), 8.30d (J=8.0, H-8), 7.97d (J=8.0, H-3'), 7.92t (J=8.0, H-7), 7.80t (J=8.0, H-6), 7.69d (J=8.0, H-6'), 7.62t (J=8.0, H-5'), 7.32t (J=8.0, H-4'), 6.67s (H-3), 3.83t, 3.67t, 3.58t, 3.33t (2H each); $\delta_c$ 201.6s (C7'), 183.1s (C1), 162.1 (COCF$_3$), 151.7s (C9), 151.4s (C4), 147.3s (C8a), 146.2s (C4a), 138.2s (C1'), 134.3d (C5'), 133.5d (C7), 131.4d (C3'), 130.8d (C8), 130.0d (C6), 128.5 (C8b), 127.5 s (C2'), 125.8d (C5), 125.2d (C4'), 123.4d (C6'), 103.3d (C3), 39.3t, 38.8t, 34.9t, 27.8t.

Basic treatment of compound 66 (NH$_3$-MeOH, cat. DMAP) directly yielded eilatin 40. Having in compound 66 all of the functionalities in the right position seems to have provided a strong and crucial driving force towards the formation of eilatin 40.

Alternatively, the last step towards the goal compound eilatin 40, could have been divided into two steps, namely, BF$_3$ etherate cyclisation to the dibenzo-1,10-phenanthroline-5,6-dione derivative 67, as described in Example VII. Specifically, compound 67 was obtained from 66 after 24 hours in CH$_2$Cl$_2$ in the presence of BF$_3$ etherate. Compound 67 was analyzed and determined to have the following physical characteristics: an amorphous yellow powder, $C_{28}H_{18}F_6N_4O_4$ m/z M, 588 (1.5%); $\delta_H$ (CDCl$_3$): 8.58d (J=8, H-1 & 10), 8.46d (J=8, H-4 & 7), 8.04t (J=8) & 7.82t (J=8) (H-2, 3, 8 & 9), 3.89m (2×2H), 3.78m (2×2H).

Sequentially, thereafter mild NH$_3$-MeOH treatment of 67 produced eilatin 40.

The readily and, very simple, biomimetic reaction described in this example, although only suggestive, points to kynuramine and o-benzoquinone, or hydroquinone, both natural products, as to the potential biosynthetic precursors of eilatin 40.

Thus, while there lave been described what are the presently contemplated preferred embodiments of the present invention, further changes and modifications could be made by those skilled in the art without departing from the scope of the invention, and it is contemplated to claim all such changes and modifications.

We claim:

1. A method for regulating cell growth, comprising: contacting a cell with an effective concentration of a compound for regulating the growth of the cell, said compound consisting essentially of Debromoshermilamine.

2. A method according to claim 1, wherein said compound further is combined with a biologically acceptable carrier.

3. A method according to claim 1, wherein said compound is further combined with a biologically acceptable carrier and said effective concentration range of said compound is 0.01 μM to 100 μM.

4. A method according to claim 3, wherein said effective concentration range is 6–32 μM.

5. A method as recited in claim 1, wherein said cell is a tumor cell, and whereby said method causes the growth of the tumor cell to suppressed.

6. A method as recited in claim 2, wherein said cell is a tumor cell, and whereby said method causes the growth of the tumor cell to be suppressed.

7. A method as recited in claim 3, wherein said cell is a tumor cell, and whereby said method causes the growth of the tumor cell to be suppressed.

8. A method as recited in claim 4, wherein said cell is a tumor cell, and whereby said method causes the growth of the tumor cell to be suppressed.

9. A method as recited in claim 5, whereby said method also induces differentiation of the tumor cell.

10. A method as recited in claim 6, whereby said method also induces differentiation of the tumor cell.

11. A method as recited in claim 7, whereby said method also induces differentiation of the tumor cell.

12. A method as recited in claim 8, whereby said method also induces differentiation of the tumor cell.

13. A method as recited in claim 5, whereby said method also induces reverse transformation of the tumor cell.

14. A method as recited in claim 6, whereby said method also induces reverse transformation of the tumor cell.

15. A method as recited in claim 7, whereby said method also induces reverse transformation of the tumor cell.

16. A method as recited in claim 8, whereby said method also induces reverse transformation of the tumor cell.

17. A method as recited in claim 1, wherein said cell is a transformed cell, and whereby said method induces reverse transformation of said transformed cell.

18. A method as recited in claim 2, wherein said cell is a transformed cell, and whereby said method induces reverse transformation of said transformed cell.

19. A method as recited in claim 3, wherein said cell is a transformed cell, and whereby said method induces reverse transformation of said transformed cell.

20. A method as recited in claim 4, wherein said cell is a transformed cell, and whereby said method induces reverse transformation of said transformed cell.

21. A method as recited in claim 1, wherein said contacting comprises contacting a plurality of cells, and whereby said method induces inhibition of proliferation of said cells.

22. A method as recited in claim 2, wherein said contacting comprises contacting a plurality of cells, and whereby said method induces inhibition of proliferation of said cells.

23. A method as recited in claim 3, wherein said contacting comprises contacting a plurality of cells, and whereby said method induces inhibition of proliferation of said cells.

24. A method as recited in claim 4, wherein said contacting comprises contacting a plurality of cells, and whereby said method induces inhibition of proliferation of said cells.

25. A method for regulating cell growth, comprising: contacting a cell with an effective concentration of a compound for regulating the growth of the cell, said compound consisting essentially of Debromoshermilamine.

26. A method according to claim 25, wherein said compound further is combined with a biologically acceptable carrier.

27. A method according to claim 25, wherein said compound is further combined with a biologically acceptable carrier and said effective concentration range of said compound is 0.01 μM to 100 μM.

28. A method according to claim 27, wherein said effective concentration range is 6–32 μM.

* * * * *